(12) United States Patent
Delikatny et al.

(10) Patent No.: US 11,813,338 B2
(45) Date of Patent: Nov. 14, 2023

(54) DIAGNOSING AND TREATING CANCER

(71) Applicant: The Trustees of the University of Pennsylvania, Philadelphia, PA (US)

(72) Inventors: Edward J. Delikatny, Havertown, PA (US); Anatoliy V. Popov, Philadelphia, PA (US); Sean P. Arlauckas, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/774,524

(22) PCT Filed: Mar. 12, 2014

(86) PCT No.: PCT/US2014/024823
§ 371 (c)(1),
(2) Date: Sep. 10, 2015

(87) PCT Pub. No.: WO2014/165216
PCT Pub. Date: Oct. 9, 2014

(65) Prior Publication Data
US 2016/0220703 A1 Aug. 4, 2016

Related U.S. Application Data

(60) Provisional application No. 61/777,319, filed on Mar. 12, 2013.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61K 31/444* | (2006.01) |
| *A61K 31/5377* | (2006.01) |
| *A61K 31/404* | (2006.01) |
| *A61K 47/55* | (2017.01) |

(52) U.S. Cl.
CPC ........ *A61K 49/0032* (2013.01); *A61K 31/404* (2013.01); *A61K 31/444* (2013.01); *A61K 31/5377* (2013.01); *A61K 47/55* (2017.08)

(58) Field of Classification Search
CPC .............. A61K 49/0032; A61K 31/404; A61K 31/444; A61K 31/5377; A61K 47/55
See application file for complete search history.

(56) References Cited

U.S. PATENT DOCUMENTS

| | | | | |
|---|---|---|---|---|
| 5,808,044 | A | * | 9/1998 | Brush ..................... C07H 21/00 536/25.31 |
| 6,534,041 | B1 | * | 3/2003 | Licha ................. A61K 49/0032 424/9.6 |
| 2002/0102208 | A1 | | 8/2002 | Chinn et al. |
| 2007/0212305 | A1 | * | 9/2007 | Klaveness .......... A61K 49/0032 424/9.341 |
| 2009/0304598 | A1 | * | 12/2009 | Gray ....................... C09B 23/06 548/219 |
| 2011/0165084 | A1 | | 7/2011 | Delikatny et al. |
| 2011/0212994 | A1 | | 9/2011 | Clem et al. |
| 2011/0250179 | A1 | | 10/2011 | Sanjuan et al. |
| 2011/0256241 | A1 | | 10/2011 | Ramirez De Molina et al. |
| 2013/0209357 | A1 | * | 8/2013 | Wang ................. A61K 49/0032 424/1.65 |

FOREIGN PATENT DOCUMENTS

| | | | | |
|---|---|---|---|---|
| EP | 1092753 A1 | * | 4/2001 | ........... C09B 23/083 |
| WO | WO-2005044923 A1 | * | 5/2005 | ........... C07D 209/10 |
| WO | WO-2012037928 A2 | * | 3/2012 | ........... A61K 31/426 |

OTHER PUBLICATIONS

Alcoceba et al. (Cancer Res. 1999, 59, 3112-3118).*
Slater et al. (J. Neurochem. 1971, 18, 943-949).*
Steiger et al. (Photographic Sci. Eng. 1981, 25, 127-138).*
Balogh et al. (Anal. Bioanal. Chem 2003, 377, 709-71).*
Wang et al. (Mol. Cryst. Liq. Cryst. 566, p. 61-66, 2012).*
Glunde et al. (The Lancet Aug. 2007, 855-857).*
Hara et al., "Choline transporter as a novel target for molecular imaging of cancer", Molecular Imaging, 5(4): 498-509, 2006.
Al-Saffar et al., "Noninvasive magnetic resonance spectroscopic pharmacodynamic markers of the choline kinase inhibitor MN58b in human carcinoma models", Cancer Res. 66(1): 427-434, 2006.
Arlauckas, Sean Philip, "Near Infrared Fluorescent Choline Kinase Inhibitors for Cancer Imaging and Therapy" (2015). Publicly Accessible Penn Dissertations. 1007. https://repository.upenn.edu/edissertations/1007.

* cited by examiner

*Primary Examiner* — Michael G. Hartley
*Assistant Examiner* — Melissa J Perreira
(74) *Attorney, Agent, or Firm* — Mark S. Cohen; PEARL COHEN ZEDEK LATZER BARATZ LLP

(57) ABSTRACT

The invention relates to compositions and methods for diagnosing as well as treating cancer diseases associated with choline kinase (ChoK). Specifically, the invention relates to a composition comprising an intrinsically fluorescent choline kinase (ChoK) inhibitor or a ChoK inhibitor operably linked to a fluorescent dye. The composition is capable of diagnosing and/or treating cancer diseases associated with ChoK.

2 Claims, 9 Drawing Sheets

DIAGNOSING AND TREATING CANCER

CROSS-REFERENCE TO RELATED APPLICATIONS

This application is a National Phase application of PCT International Application No. PCT/US14/24823, International filing date Mar. 12, 2015, which claims priority to and the benefit of U.S. Provisional Patent Application 61/777,319, filed Mar. 12, 2013, all of which are incorporated by reference herein in their entirety.

GOVERNMENT INTEREST

The invention described in this application was supported by the United States Department of Defense, Grant Number BC076631. The United States Government has certain rights in this application.

FIELD OF THE INVENTION

The invention relates to compositions and methods for diagnosing as well as treating cancer diseases associated with choline kinase (ChoK). Specifically, the invention relates to a composition comprising an intrinsically fluorescent choline kinase (ChoK) inhibitor or a ChoK inhibitor operably linked to a fluorescent dye. The composition is capable of diagnosing and/or treating cancer diseases associated with ChoK.

BACKGROUND OF THE INVENTION

Choline kinase (ChoK) deregulation is associated with greater malignancy in a number of human cancers. ChoK catalyzes the conversion of choline to phosphocholine (PC), the first step in biosynthesis of the major membrane phospholipid phosphatidylcholine (PtdCho). Elevated ChoK activity has been correlated with histological tumor grade in breast cancer, and corresponds to an overall poorer prognosis in lung cancer. Heightened expression has been found to be inducible by carcinogens and a number of oncogenes, and has been reported in bladder, colon, lung, ovarian, and prostate tumors. Alterations in the profile of choline metabolites are detectable by magnetic resonance spectroscopy (MRS), but because there are also competing catabolic contributions from the phospholipases, the activity and concentration of ChoK cannot be definitively determined in a clinical setting.

Inhibitors of ChoK have been demonstrated to slow tumor growth and improve patient response to other drugs such as 5-fluorouracil. Importantly, ChoK inhibition induces apoptosis in tumorigenic cells, but has minimal effects on normal cells.

However, no single compound can simultaneously diagnose and treat cancer diseases associated with ChoK.

Accordingly, there exists a need to develop improved compositions and methods to diagnose and treat cancer diseases associated with ChoK.

SUMMARY OF THE INVENTION

In one aspect, the invention provides a composition comprising a choline kinase (ChoK) inhibitor, wherein said composition is capable of diagnosing and/or treating cancer diseases associated with ChoK.

In another aspect, the invention provides a composition comprising an intrinsically fluorescent choline kinase (ChoK) inhibitor or ChoK inhibitor operably linked to a fluorescent dye, wherein said composition is capable of diagnosing and/or treating cancer diseases associated with ChoK.

In some embodiments, the invention provides a composition capable of diagnosing and/or treating cancer diseases associated with ChoK, wherein said composition comprising a compound of Formula I,

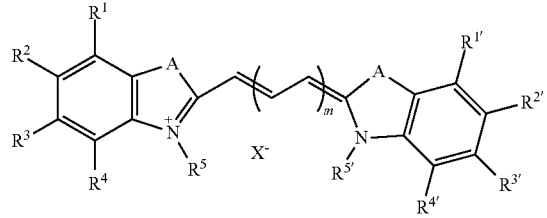

(I)

wherein:
- $R^1$, $R^2$, $R^3$, $R^4$, $R^{1'}$, $R^{2'}$, $R^{3'}$, and $R^{4'}$ are independently selected from H, halo, $C_{1-6}$ alkyl, $C_{2-6}$ alkenyl, and $C_{1-6}$ haloalkyl, or any two of $R^1$, $R^2$, $R^3$, and $R^4$ or any two of $R^{1'}$, $R^{2'}$, $R^{3'}$, and $R^{4'}$ form a 5- or 6-membered ring;
- $R^5$ and $R^{5'}$ are independently selected from $C_{1-6}$ alkyl and $C_{1-6}$ omega-hydroxyalkyl;
- m is 1, 2, 3, 4, or 5;
- A is O, S, or $C(CH_3)_2$; and
- $X^-$ is the conjugate base of a pharmaceutically suitable organic or inorganic acid.

In some embodiments, the invention provides a composition capable of diagnosing and/or treating cancer diseases associated with ChoK, wherein said composition comprising a compound of Formula II,

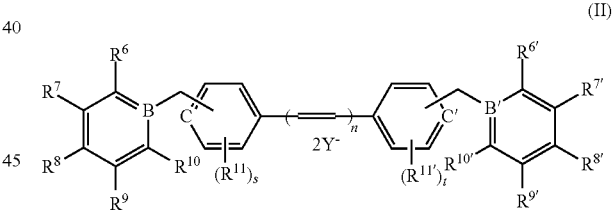

(II)

wherein:
- $R^6$, $R^7$, $R^8$, $R^9$, $R^{10}$, $R^{6'}$, $R^{9'}$, and $R^{10'}$ are independently selected from H, halo, $C_{1-6}$ alkyl, $C_{2-6}$ alkenyl, $C_{1-6}$ haloalkyl, and $NR^pR^q$, wherein $R^p$ and $R^q$ are independently selected from H, $C_{1-8}$ g alkyl, $C_{3-6}$ cycloalkyl, aryl, heteroaryl, aryl-$C_{1-5}$ alkyl, and heteroaryl-$C_{1-5}$ alkyl, wherein said $C_{1-8}$ alkyl, $C_{3-6}$ cycloalkyl, aryl, heteroaryl, aryl-$C_{1-5}$ alkyl, and heteroaryl-$C_{1-5}$ alkyl are optionally mono- or polysubstituted with substituents independently selected from halo, OH, O—$C_{1-3}$ alkyl, and $C_{1-3}$ haloalkyl, or $R^p$ and $R^q$, together with the N atom to which they are attached, form a 3-8 membered cycloheteroalkyl group, each optionally substituted with 1, 2, or 3 substituents independently selected from halo and $C_{1-6}$ alkyl;
- or any two of $R^6$, $R^7$, $R^8$, $R^9$, and $R^{10}$ or any two of $R^{6'}$, R, and $R^{10'}$ form a 5- or 6-membered ring;
- $R^{11}$ and $R^{11'}$ are independently selected from H, halo, and $C_{1-6}$ alkyl;

B, B', C, and C' are independent selected from C and $N^+$;

n is 0, 1, 2, 3, or 4;

s and t are independently selected from 0, 1, 2, 3, and 4; and $Y^-$ is the conjugate base of a pharmaceutically suitable organic or inorganic acid.

In some embodiments, n is 1, 2, 3, or 4.

In yet another aspect, the invention provides a method for diagnosing and/or treating a cancer disease associated with choline kinase (ChoK), the method comprising: administering to a subject an effective amount of a composition comprising a choline kinase (ChoK) inhibitor, wherein said composition is capable of diagnosing and/or treating cancer diseases associated with ChoK.

In yet another aspect, the invention provides a method for diagnosing and/or treating a cancer disease associated with choline kinase (ChoK), the method comprising: administering to a subject an effective amount of a composition comprising a choline kinase (ChoK) inhibitor operably linked to a fluorescent dye, wherein said composition is capable of diagnosing and/or treating cancer diseases associated with ChoK.

In some embodiments, the invention provides a method for diagnosing and/or treating a cancer disease associated with choline kinase (ChoK), the method comprising: administering to a subject an effective amount of a composition comprising a compound of Formula I,

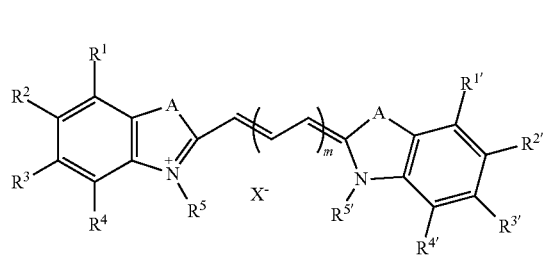

(I)

wherein:

$R^1$, $R^2$, $R^3$, $R^4$, $R^{1'}$, $R^{2'}$, $R^{3'}$, and $R^{4'}$ are independently selected from H, halo, $C_{1-6}$ alkyl, $C_{2-6}$ alkenyl, and $C_{1-6}$ haloalkyl, or any two of $R^1$, $R^2$, $R^3$, and $R^4$ or any two of $R^{1'}$, $R^{2'}$, $R^{3'}$, and $R^{4'}$ form a 5- or 6-membered ring;

$R^5$ and $R^{5'}$ are independently selected from $C_{1-6}$ alkyl and $C_{1-6}$ omega-hydroxyalkyl;

m is 1, 2, 3, 4, or 5;

A is O, S, or $C(CH_3)_2$; and $X^-$ is the conjugate base of a pharmaceutically suitable organic or inorganic acid.

In some embodiments, the invention provides a method for diagnosing and/or treating a cancer disease associated with choline kinase (ChoK), the method comprising: administering to a subject an effective amount of a composition comprising a compound of Formula II,

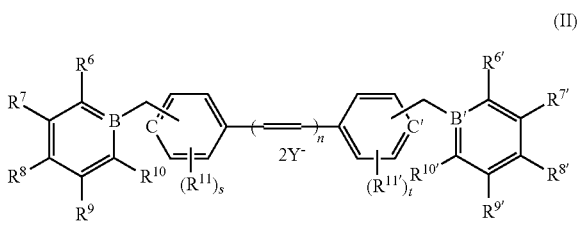

(II)

wherein:

$R^6$, $R^7$, $R^8$, $R^9$, $R^{10}$, $R^{6'}$, $R^{7'}$, $R^{8'}$, $R^{9'}$, and $R^{10'}$ are independently selected from H, halo, $C_{1-6}$ alkyl, $C_{2-6}$ alkenyl, $C_{1-6}$ haloalkyl, and $NR^pR^q$, wherein $R^p$ and $R^q$ are independently selected from H, $C_{1-8}$ alkyl, $C_{3-6}$ cycloalkyl, aryl, heteroaryl, aryl-$C_{1-5}$ alkyl, and heteroaryl-$C_{1-5}$ alkyl, wherein said $C_{1-8}$ alkyl, $C_{3-6}$ cycloalkyl, aryl, heteroaryl, aryl-$C_{1-5}$ alkyl, and heteroaryl-$C_{1-5}$ alkyl are optionally mono- or polysubstituted with substituents independently selected from halo, OH, O—$C_{1-3}$ alkyl, and $C_{1-3}$ haloalkyl, or $R^p$ and $R^q$, together with the N atom to which they are attached, form a 3-8 membered cycloheteroalkyl group, each optionally substituted with 1, 2, or 3 substituents independently selected from halo and $C_{1-6}$ alkyl;

or any two of $R^6$, $R^7$, $R^8$, $R^9$, and $R^{10}$ or any two of $R^{6'}$, $R^{9'}$, and $R^{10'}$ form a 5- or 6-membered ring;

$R^{11}$ and $R^{11'}$ are independently selected from H, halo, and $C_{1-6}$ alkyl;

B, B', C, and C' are independent selected from C and $N^+$;

n is 0, 1, 2, 3, or 4;

s and t are independently selected from 0, 1, 2, 3, and 4; and $Y^-$ is the conjugate base of a pharmaceutically suitable organic or inorganic acid.

In some embodiments, n is 1, 2, 3, or 4.

In another aspect, the invention provides a method for diagnosing a cancer disease associated with choline kinase (ChoK), the method comprising: administering to a subject an effective amount of a composition comprising a compound of Formula I, wherein variables $R^1$, $R^2$, $R^3$, $R^4$, $R^{1'}$, $R^{2'}$, $R^{3'}$, $R^{4'}$, $R^5$, $R^{5'}$, m, A, and $X^-$ can be defined anywhere herein.

In another aspect, the invention provides a method for treating a cancer disease associated with choline kinase (ChoK), the method comprising: administering to a subject an effective amount of a composition comprising a compound of Formula I, wherein variables $R^1$, $R^2$, $R^3$, $R^4$, $R^{1'}$, $R^{2'}$, $R^{3'}$, $R^{4'}$, $R^5$, $R^{5'}$, m, A, and $X^-$ can be defined anywhere herein.

In yet another aspect, the invention provides a method for diagnosing a cancer disease associated with choline kinase (ChoK), the method comprising: administering to a subject an effective amount of a composition comprising a compound of Formula II, wherein variables $R^6$, $R^7$, $R^8$, $R^9$, $R^{10}$, $R^{6'}$, $R^{7'}$, $R^{8'}$, $R^{9'}$, $R^{10'}$, $R^{11}$, $R^{11'}$, B, B', C, C', n, s, t, and $Y^-$ can be defined anywhere herein.

In yet another aspect, the invention provides a method for treating a cancer disease associated with choline kinase (ChoK), the method comprising: administering to a subject an effective amount of a composition comprising a compound of Formula II, wherein variables $R^6$, $R^7$, $R^8$, $R^9$, $R^{10}$, $R^{6'}$, $R^{7'}$, $R^{8'}$, $R^{9'}$, $R^{10'}$, $R^{11}$, $R^{11'}$ B, B', C, C', n, s, t, and $Y^-$ can be defined anywhere herein.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
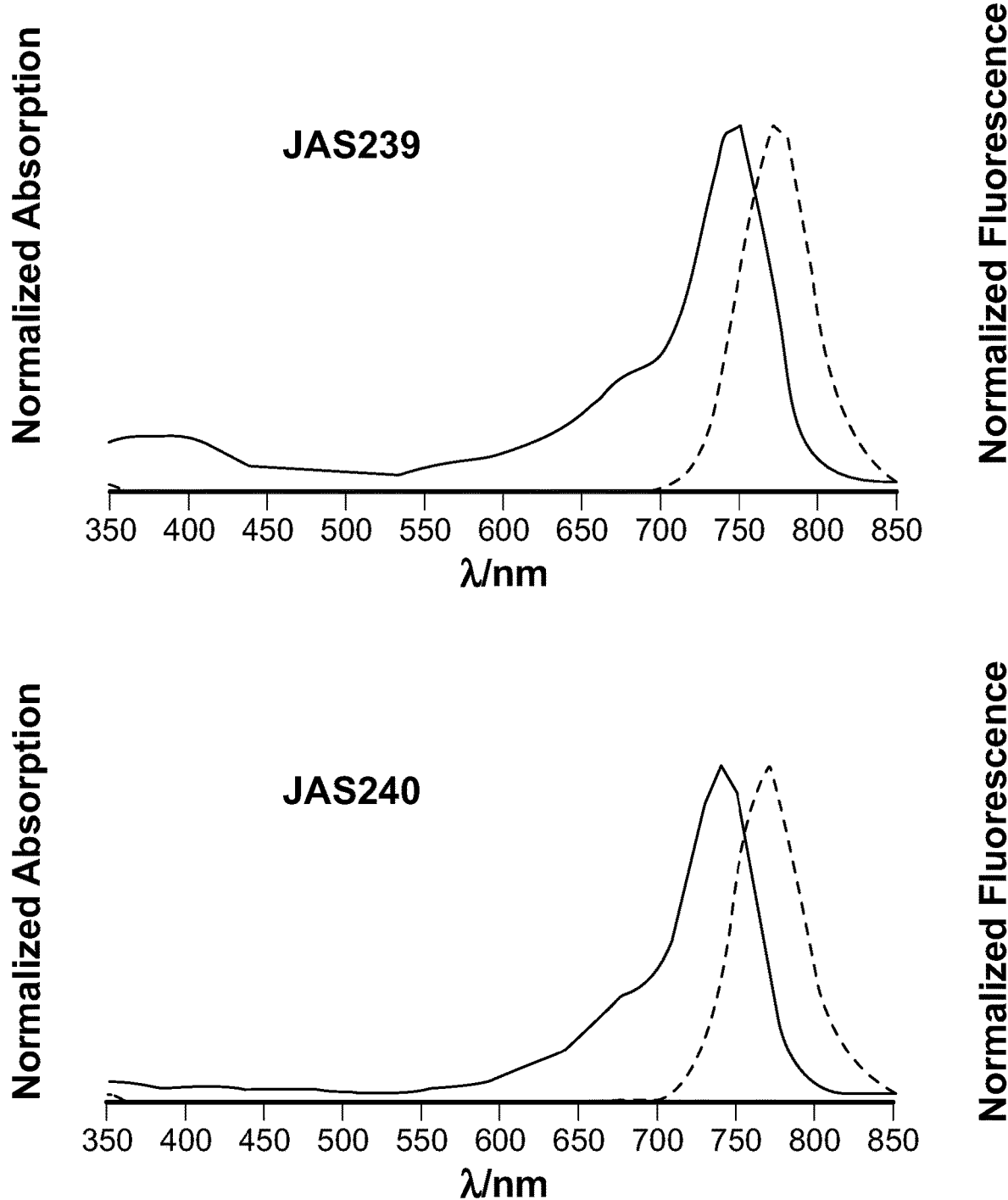
FIG. 1 depicts absorption and emission spectra Top) JAS239, and Bottom) JAS240 in ethanol at room temperature, demonstrating fluorescence in the NW range.

The invention relates to compositions and methods for diagnosing as well as treating cancer diseases associated with choline kinase (ChoK). Specifically, the invention relates to a composition comprising an intrinsically fluorescent ChoK inhibitor (e.g., an intrinsically fluorescent bis-heterocyclic ChoK inhibitor), said composition capable of diagnosing and/or treating cancer diseases associated with ChoK.

The invention further relates to compositions and methods for diagnosing as well as treating cancer diseases associated with choline kinase (ChoK). Specifically, the invention relates to a composition comprising a ChoK inhibitor (e.g., a bis-heterocyclic ChoK inhibitor) having inherent fluorescence or operably linked to a fluorescent dye, said composition capable of diagnosing and/or treating cancer diseases associated with ChoK. In some embodiments, the compositions can be used for intra-operative imaging, and thus function as intra-operative probes.

The inventors of the instant application have found that an intrinsically fluorescent ChoK inhibitor or a structural hybrid of a ChoK inhibitor (e.g., hemicholinium-3 or MN58B) and a fluorescent dye (e.g., indocyanine dye) can act as diagnostic fluorescent agent to provide diagnosis of a cancer and as therapeutic agent to treat the cancer.

The composition of the invention may include features that are effective for ChoK inhibition. These features include, for example, but are not limited to, bis-heterocyclic structure which may be symmetric or non-symmetric, quarternary ammonium groups, water solubility, and an aliphatic spacer.

The invention is applicable to any ChoK inhibitor, including, for example, a bis-heterocyclic ChoK inhibitor, known to one skilled in the art. Examples of a bis-heterocyclic ChoK inhibitor include, but are not limited to, hemicholinium-3 (HC-3), and 1,4-[4-4'-Bis-{[4-(dimethylamine)pyridinium-1-yl]methyl}diphenyl]butane dibromide (MN58b).

In some embodiments, the ChoK inhibitor can be hemicholinium-3 (HC-3). In other embodiments, the ChoK inhibitor can be (1,4-[4-4'-Bis-{[4-(dimethylamine)pyridinium-1-yl]methyl}diphenyl]butane dibromide) (MN58b).

Any suitable dye, known to one skilled in the art, can be used. Examples of a dye include, but are not limited to, a carbocyanine dye, an indocyanine dye, a near infrared fluorophore, including fluorescent porphyrins such as for example, a pyropheophorbide a.

In some embodiments, the fluorescent dye can be a carbocyanine dye. In other embodiments, the fluorescent dye can be an indocyanine dye. In certain embodiments, the fluorescent dye can be a near infrared fluorophore. In some embodiments, the fluorescent dye can be a pyropheophorbide a. In some embodiments, the bis-heterocyclic ChoK inhibitor can be chemically conjugated to the fluorescent dye.

The ChoK inhibitor can be linked to the dye by any technique known to one skilled in the art. In one embodiment, the ChoK inhibitor is chemically conjugated to the dye. Any suitable conjugation methods, known to one of skilled in the art, can be used.

In some embodiments, the cancer disease associated with ChoK can be a breast cancer.

In some embodiments, the cancer disease associated with ChoK can be a lung cancer, a bladder cancer, a prostate cancer, a colorectal cancer, an ovarian cancer, a non-small cell lung cancer, or a gastrointestinal cancer, or any other cancer in which ChoK is expressed.

The composition of the invention may include a compound of Formula I,

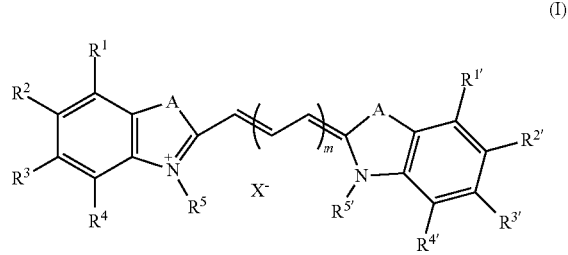

in which

R$^1$, R$^2$, R$^3$, R$^4$, R$^{1'}$, R$^{2'}$, R$^{3'}$, and R$^{4'}$ are independently selected from H, halo, C$_{1-6}$ alkyl, C$_{2-6}$ alkenyl, and C$_{1-6}$ haloalky, or any two of R$^1$, R$^2$, R$^3$, and R$^4$ or any two of R$^{1'}$, R$^{2'}$, R$^{3'}$, and R$^{4'}$ form a 5- or 6-membered ring;

R$^5$ and R$^{5'}$ are independently selected from C$_{1-6}$ alkyl and C$_{1-6}$ omega-hydroxyalkyl;

m is 1, 2, 3, 4, or 5;

A is O, S, or C(CH$_3$)$_2$; and

X$^-$ is the conjugate base of a pharmaceutically suitable organic or inorganic acid.

In some embodiments, R$^1$, R$^2$, R$^3$, R$^4$, R$^{1'}$, R$^{2'}$, R$^{3'}$, and R$^{4'}$ all are H.

In some embodiments, R$^5$ and R$^{5'}$ both are alkyl.

In some embodiments, R$^5$ and R$^{5'}$ both are methyl.

In some embodiments, R$^5$ and R$^{5'}$ both are omega-hydroxyalkyl.

In some embodiments, R$^5$ and R$^{5'}$ both are 2-hydroxyethyl.

In some embodiments, m is 3.

In some embodiments, A is C(CH$_3$)$_2$.

In some embodiments, X$^-$ is F. In other embodiments, X$^-$ is Br$^-$. In certain embodiments, X$^-$ is CF.

In certain embodiments, the compound of Formula I is

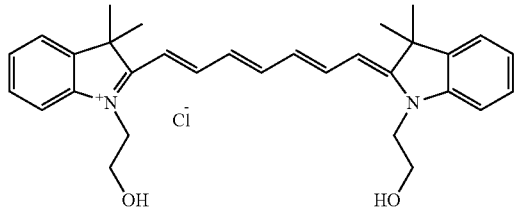 [SMILES: CC1(C)C(/C=C/C=C/C=C/C=C2\N(CCO)c3ccccc3C2(C)C)=[N+](CCO)c2ccccc21 ; Cl]

(1-(2-hydroxyethyl)-2-((1E,3E,5E)-7-((Z/E)-1-(2-hydroxyethyl)-3,3-dimethylindolin-2-ylidene)hepta-1,3,5-trien-1-yl)-3,3-dimethyl-3H-indol-1-ium chloride (JAS239)).

In other embodiments, the compound of Formula I is

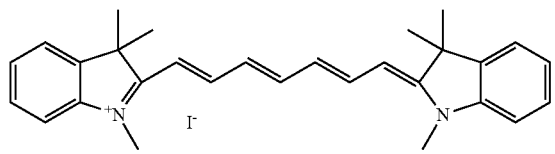 [SMILES: CN1\C(=C/C=C/C=C/C=C/C2=[N+](C)c3ccccc3C2(C)C)C(C)(C)c2ccccc21 ; [I-]]

(1,3,3-trimethyl-2-((1E,3E,5E)-7-((Z/E)-1,3,3-trimethylindolin-2-ylidene)hepta-1,3,5-trien-1-yl)-3H-indol-1-ium iodide (JAS240)).

The composition of the invention may include a compound of Formula II,

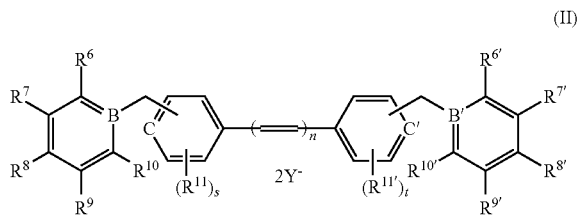

wherein:

R$^6$, R$^7$, R$^8$, R$^9$, R$^{10}$, R$^{6'}$, R$^{7'}$, R$^{8'}$, R$^{9'}$, and R$^{10'}$ are independently selected from H, halo, C$_{1-6}$ alkyl, C$_{2-6}$ alkenyl, C$_{1-6}$ haloalkyl, and NR$^p$R$^q$, wherein R$^p$ and R$^q$ can be independently selected from H, C$_{1-8}$ alkyl, C$_{3-6}$ cycloalkyl, aryl, heteroaryl, aryl-C$_{1-5}$ alkyl, and heteroaryl-C$_{1-5}$ alkyl, wherein said C$_{1-8}$ alkyl, C$_{3-6}$ cycloalkyl, aryl, heteroaryl, aryl-C$_{1-5}$ alkyl, and heteroaryl-C$_{1-5}$ alkyl are optionally mono- or polysubstituted with substituents independently selected from halo, OH, O—C$_{1-3}$ alkyl, and C$_{1-3}$ haloalkyl, or R$^p$ and R$^q$, together with the N atom to which they are attached, form a 3-8 membered cycloheteroalkyl group, each optionally substituted with 1, 2, or 3 substituents independently selected from halo and C$_{1-6}$ alkyl;

or any two of R$^6$, R$^7$, R$^8$, R$^9$, and R$^{10}$ or any two of R$^{6'}$, R$^{7'}$, R$^{9'}$, and R$^{10'}$ form a 5- or 6-membered ring;

R$^{11}$ and R$^{11'}$ are independently selected from H, halo, and C$_{1-6}$ alkyl;

B, B', C, and C' are independent selected from C and N$^+$;

n is 0, 1, 2, 3, or 4;

s and t are independently selected from 0, 1, 2, 3, and 4; and

Y$^-$ is the conjugate base of a pharmaceutically suitable organic or inorganic acid.

In some embodiments, n is 1, 2, 3, or 4.

In some embodiments, n is 0.

In some embodiments, the compound of Formula II has Formula III

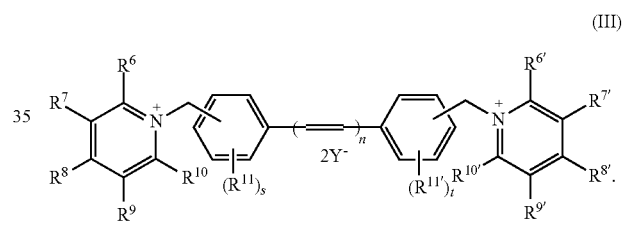

In some embodiments, n is 1, 2, 3, or 4.

In some embodiments, n is 0.

In some embodiments, the compound of Formula II has Formula IV

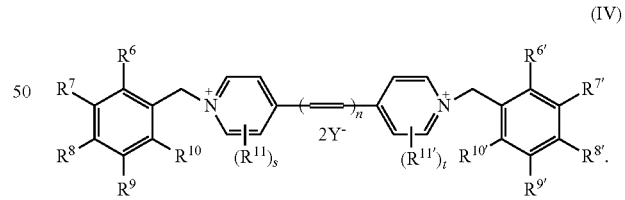

In some embodiments, R$^6$, R$^7$, R$^9$, R$^{10}$, R$^{6'}$, R$^{7'}$, R$^{9'}$, and R$^{10'}$ all are H.

In some embodiments, R$^8$ is NR$^p$R$^q$. In certain embodiments, R$^p$ and R$^q$, together with the N atom to which they are attached, form a 5-7 membered cycloheteroalkyl group. In other embodiments, R$^p$ and R$^q$, together with the N atom to which they are attached, form a pyrrolidino, piperidino, or perhydroazepino group.

In some embodiments, R$^8$ is N(CH$_3$)$_2$. In other embodiments, R$^8$ is NHR$^q$. In certain embodiments, R$^8$ is NH$_2$.

In some embodiments, R$^{11}$ and R$^{11'}$ are both H.

In other embodiments, n is 2.

In some embodiments, Y⁻ is Br⁻.

In some embodiments, the compound of Formula II has Formula VI

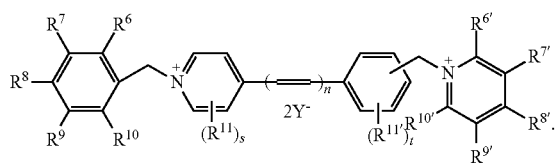

In some embodiments, n is 1, 2, 3, or 4.

In some embodiments, n is 0.

In some embodiments, $R^6$, $R^7$, $R^9$, $R^{10}$, $R^{6'}$, $R^{7'}$, $R^{9'}$, and $R^{10'}$ all are H.

In some embodiments, $R^8$ is $NR^pR^q$. In certain embodiments, $R^p$ and $R^q$, together with the N atom to which they are attached, form a 5-7 membered cycloheteroalkyl group.

In other embodiments, $R^p$ and $R^q$, together with the N atom to which they are attached, form a pyrrolidino, piperidino, or perhydroazepino group.

In some embodiments, $R^8$ is $N(CH_3)_2$. In other embodiments, $R^8$ is $NHR^q$. In certain embodiments, $R^8$ is $NH_2$.

In some embodiments, $R^{8'}$ is $NR^{p'}R^{q'}$. In certain embodiments, $R^{p'}$ and $R^{q'}$, together with the N atom to which they are attached, form a 5-7 membered cycloheteroalkyl group. In other embodiments, $R^{p'}$ and $R^{q'}$, together with the N atom to which they are attached, form a pyrrolidino, piperidino, or perhydroazepino group.

In some embodiments, $R^{8'}$ is $N(CH_3)_2$. In other embodiments, $R^{8'}$ is $NHR^{q'}$. In certain embodiments, $R^{8'}$ is $NH_2$.

In some embodiments, $R^{11}$ and $R^{11'}$ are both H.

In other embodiments, n is 2.

In some embodiments, Y⁻ is Br⁻.

In some embodiments, the compound of Formula II is

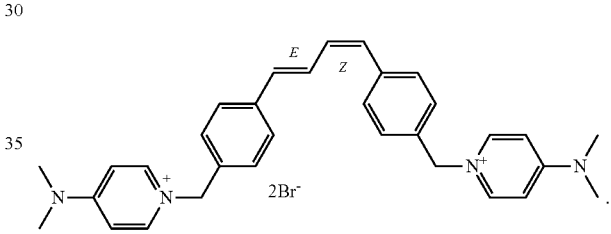

(1,1'-(((1Z,3Z)-buta-1,3-diene-1,4-diyl)bis(4,1-phenylene))bis(methylene))bis(4-(dimethylamino)pyridin-1-ium) bromide).

In some embodiments, the compound of Formula II is

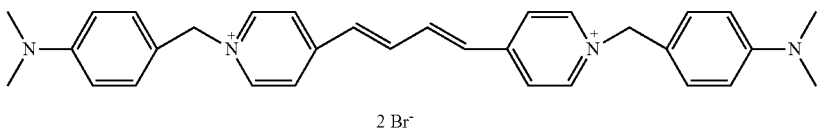

(1,1'-(((1E,3E)-buta-1,3-diene-1,4-diyl)bis(4,1-phenylene))bis(methylene))bis(4-(dimethylamino)pyridin-1-ium) bromide).

In some embodiments, the compound of Formula II is

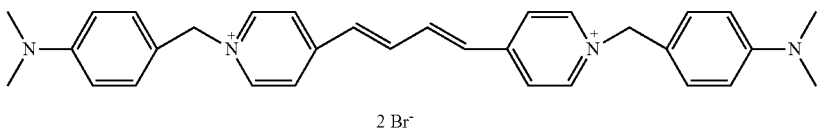

(1,1'-(((1Z,3E)-buta-1,3-diene-1,4-diyl)bis(4,1-phenylene))bis(methylene))bis(4-(dimethylamino)pyridin-1-ium) bromide).

In some embodiments, the compound of Formula II is

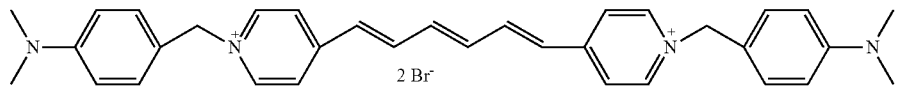

(4,4'-(buta-1,3-diene-1,4-diyl)bis(1-(4-(dimethylamino)benzyl)pyridin-1-ium) bromide).

In some embodiments, the compound of Formula II can be (4,4'-(hexa-1,3,5-triene-1,6-diyl)bis(1-(4-(dimethyl-amino)benzyl)pyridin-1-ium) bromide).

The composition of the invention may include a compound of Formula V,

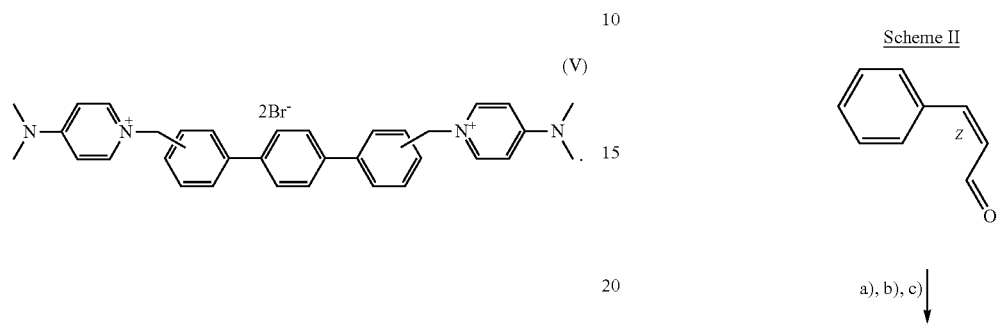

(V)

The compounds of Formula II can be synthesized by the reactions as described in Schemes II and III:

Scheme II

Synthesis

The compounds of Formula I can be prepared by a two step synthesis as described in Scheme I:

Scheme I

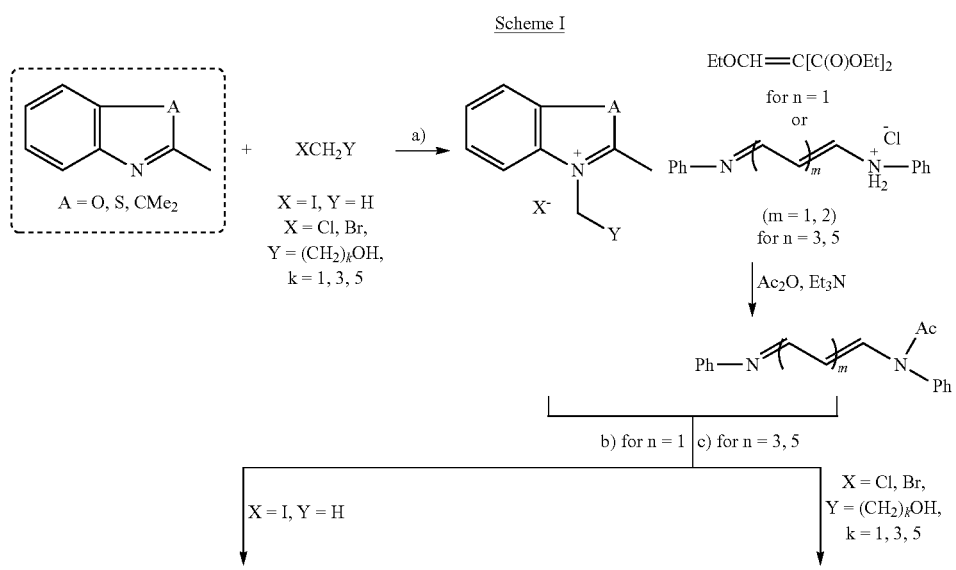

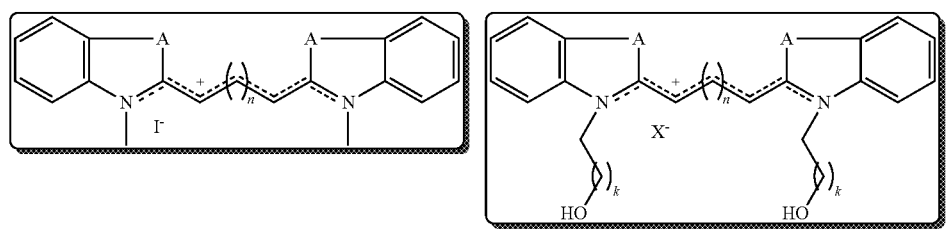

A = O, S, CMe$_2$; n = 1, 3, 5; k = 1, 3, 5; X = Cl, Br a) EtOH, 140 C., 2 h, autoclave; b) Et$_3$N EtOH, 3 h; c) AcONa, EtOH, reflux, 5 h

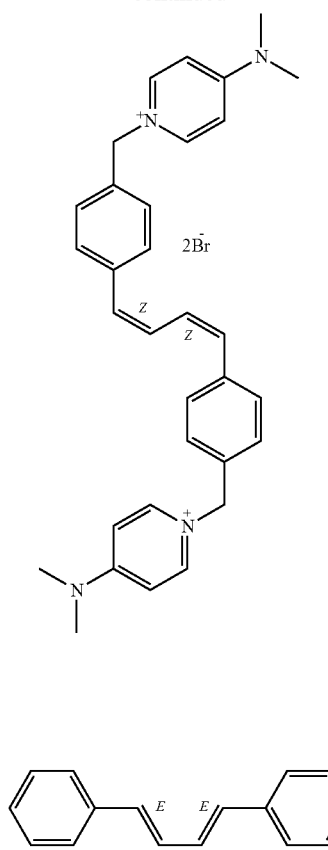
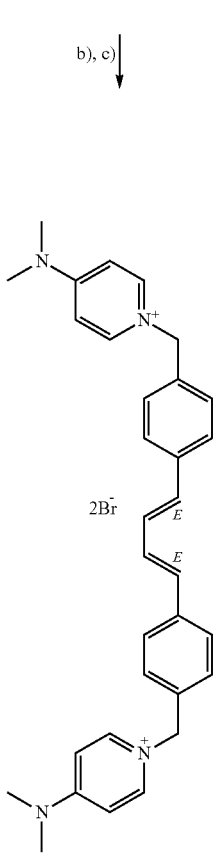
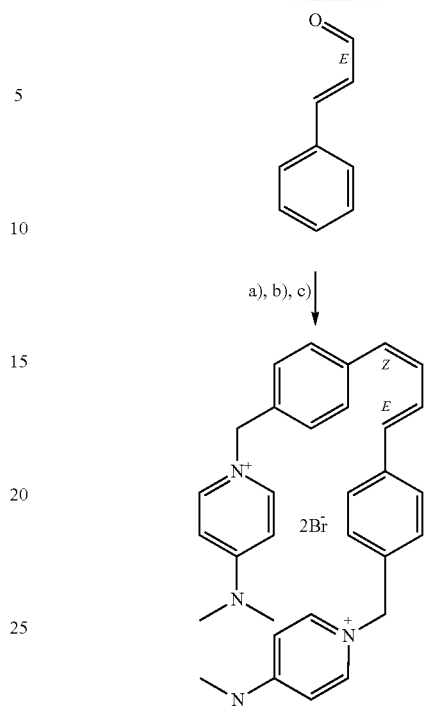
a) 1. (EtO)$_4$Si; 2,6-Cl$_2$C$_6$H$_3$SO$_2$NH$_2$; 2. BnPh$_3$PBr, LDA, THF, -78° C.-rt; b) 1,3,5-trioxane, HBr, AcOH, reflux; c) DMAP.
Scheme III
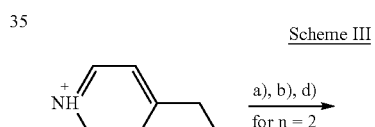
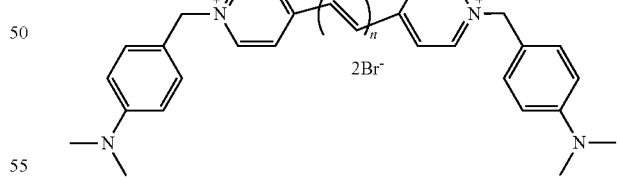
n = 2, 3
a) 1. NaOH, 2) PPh$_3$; b) glyoxal = (COH)$_2$; c) [(EtO)$_2$PCH$_2$CH=]$_2$, tBuOK; d) p-Me$_2$NC$_6$H$_4$CH$_2$Br.
The compound of formula V can be prepared according to Scheme IV.

Scheme IV

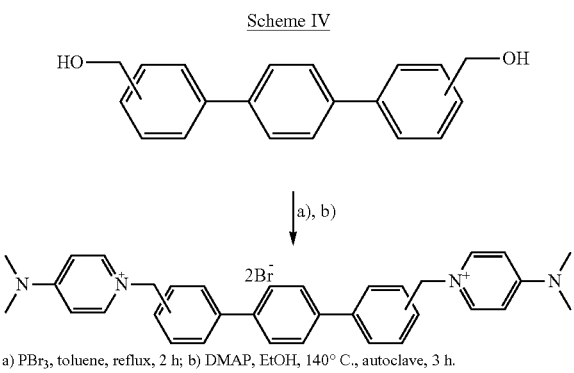

a) PBr₃, toluene, reflux, 2 h; b) DMAP, EtOH, 140° C., autoclave, 3 h.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In some embodiments, the

moiety or formulas II-IV and VI can indicate a plural of double bonds as recognized by a person skilled in the art. For example, when n is 2, the

moiety includes two double bonds. When n is 3, the

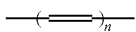

moiety includes three double bonds. In some embodiments, all double bonds in the

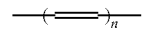

moiety of formulas II-IV and VI can be in E configuration. In other embodiments, all double bonds in the

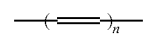

moiety of formulas II-IV can be in Z configuration. In some embodiments, the double bonds in the

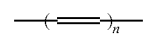

moiety of formulas II-IV and VI can be a mixture of double bonds having Z configuration and double bonds having E configuration. For example, when n is 3, two double bonds in the

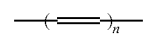

moiety can be in Z configuration and one double bond can be in E configuration, or two double bonds in the

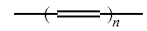

moiety can be in E configuration and one double bond can be in Z configuration.

In some embodiments, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 6, from 1 to about 4, or from 1 to about 3 carbon atoms.

In some embodiments, "alkenyl" refers to an alkyl group having one or more double carbon-carbon bonds. Example alkenyl groups include ethenyl, propenyl, and the like.

In some embodiments, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

In some embodiments, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings can be attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

In some embodiments, "cycloheteroalkyl" refers to a non-aromatic heterocycle where one or more of the ring-forming atoms is a heteroatom such as an O, N, or S atom. Cycloheteroalkyl groups can include mono- or polycyclic (e.g., having 2, 3 or 4 fused rings) ring systems as well as spirocycles. Example cycloheteroalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of cycloheteroalkyl are moieties that have one or more aromatic rings fused (i.e., having a bond in common with) to the nonaromatic heterocyclic ring, for example phthalimidyl, naphthalimidyl, and benzo derivatives of heterocycles.

In some embodiments, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

In some embodiments, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

In some embodiments, "halo" or "halogen" includes fluoro, chloro, bromo, and iodo.

In some embodiments, the term "substituted" refers to the replacement of a hydrogen moiety with a non-hydrogen moiety in a molecule or group.

In some embodiments, a "5- or 6-membered ring" refers to a saturated, unsaturated, or aromatic carbocycle or heterocycle. In some embodiments, the 5- or 6-membered ring can form a fused ring system (i.e., having a bond in common) with another ring (e.g., benzene or pyridine). Exemplified fused ring systems include, but are not limited to, indole, 1-benzofuran, naphthalene, and the like.

In some embodiments, "compound," as used herein is meant to include all stereoisomers, geometric isomers, tautomers, and isotopomers of the structures depicted. All compounds are also meant to include solvated, or hydrated forms.

In some embodiments, the term "conjugate base of a pharmaceutically suitable organic or inorganic acid" refers to the ion formed when a pharmaceutically suitable organic or inorganic acid loses a hydrogen ion, e.g. fluoride, chloride, bromide, iodide, sulfate, phosphate, benzoate, hexafluorophosphate, methanesulfonate, p-tolylsulfonate, trifluoromethylsulfonate, acetate, nitrate, maleate, fumarate, lactate, citrate, tartrate, succinate or gluconate.

The invention provides methods of diagnosing and/or treating a disease or condition, comprising administering to a mammal in need thereof an effective amount of a ChoK inhibitor.

The invention further provides methods of diagnosing and/or treating a disease or condition, comprising administering to a mammal in need thereof an effective amount of an intrinsically fluorescent ChoK inhibitor or a ChoK inhibitor operably linked to a fluorescent dye, or combination thereof.

In some embodiments, the ChoK inhibitor can be hemicholinium-3 (HC-3). In other embodiments, the ChoK inhibitor can be (1,4-[4-4'-Bis-{[4-(dimethyl amine)pyridinium-1-yl]methyl}diphenyl]butane dibromide) (MN-58b).

In some embodiments, the fluorescent dye can be a carbocyanine dye. In other embodiments, the fluorescent dye can be an indocyanine dye. In certain embodiments, the fluorescent dye can be a near infrared fluorophore. In some embodiments, the fluorescent dye can be a pyropheophorbide a. In some embodiments, the ChoK inhibitor can be chemically conjugated to the fluorescent dye.

The invention provides methods of diagnosing and/or treating a cancer disease associated with choline kinase (ChoK), the method comprising: administering to a subject an effective amount of a composition comprising a compound of Formula I,

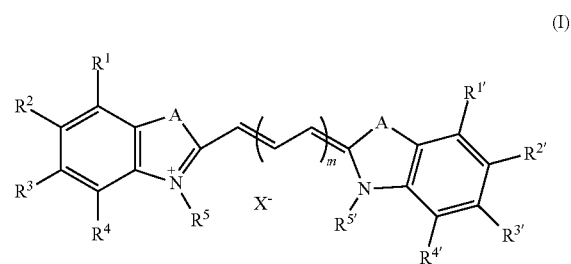

(I)

in which
$R^1$, $R^2$, $R^3$, $R^4$, $R^{1'}$, $R^{2'}$, $R^{3'}$, and $R^{4'}$ are independently selected from H, halo, $C_{1-6}$ alkyl, $C_{2-6}$ alkenyl, and $C_{1-6}$ haloalkyl, or any two of $R^1$, $R^2$, $R^3$, and $R^4$ or any two of $R^{1'}$, $R^{2'}$, $R^{3'}$, and $R^{4'}$ form a 5- or 6-membered ring;
$R^5$ and $R^{5'}$ are independently selected from $C_{1-6}$ alkyl and $C_{1-6}$ omega-hydroxyalkyl;
m is 1, 2, 3, 4, or 5;
A is O, S, or $C(CH_3)_2$; and
$X^-$ is the conjugate base of a pharmaceutically suitable organic or inorganic acid.

In some embodiments, $R^1$, $R^2$, $R^3$, $R^4$, $R^{1'}$, $R^{2'}$, $R^{3'}$, and $R^{4'}$ all are H.

In some embodiments, $R^5$ and $R^{5'}$ both are alkyl.

In some embodiments, $R^5$ and $R^{5'}$ both are methyl.

In some embodiments, $R^5$ and $R^{5'}$ both are omega-hydroxyalkyl.

In some embodiments, $R^5$ and $R^{5'}$ both are 2-hydroxyethyl.

In some embodiments, m is 3.

In some embodiments, A is $C(CH_3)_2$.

In some embodiments, $X^-$ is F. In other embodiments, $X^-$ is $Br^-$. In certain embodiments, $X^-$ is $Cl^-$.

In certain embodiments, the compound of Formula I is

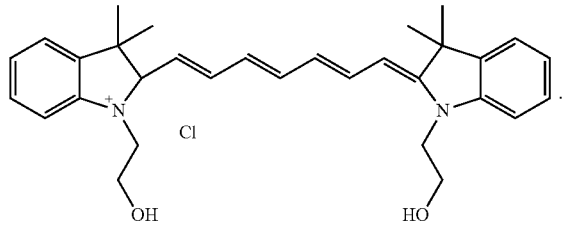

(JAS239)

In other embodiments, the compound of Formula I is (JAS240)

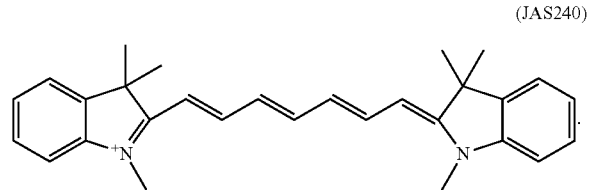 [SMILES: CN1\C(=C/C=C/C=C/C=C/C2=[N+](C)c3ccccc3C2(C)C)C(C)(C)c2ccccc21]

The invention provides methods of diagnosing and/or treating a cancer disease associated with choline kinase (ChoK), the method comprising: administering to a subject an effective amount of a composition comprising a compound of Formula II, (II)

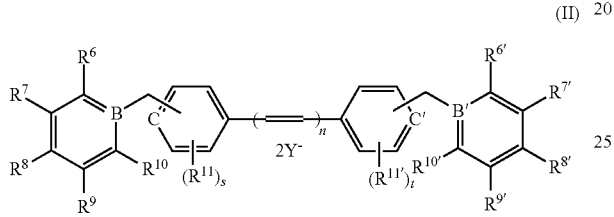

in which:

R$^6$, R$^7$, R$^8$, R$^9$, R$^{10}$, R$^{6'}$, R$^{7'}$, R$^{8'}$, R$^{9'}$, and R$^{10'}$ are independently selected from H, halo, C$_{1-6}$ alkyl, C$_{2-6}$ alkenyl, C$_{1-6}$ haloalkyl, and NR$^p$R$^q$, wherein R$^p$ and R$^q$ are independently selected from H, C$_{1-8}$ alkyl, C$_{3-6}$ cycloalkyl, aryl, heteroaryl, aryl-C$_{1-5}$ alkyl, and heteroaryl-C$_{1-5}$ alkyl, wherein said C$_{1-8}$ alkyl, C$_{3-6}$ cycloalkyl, aryl, heteroaryl, aryl-C$_{1-5}$ alkyl, and heteroaryl-C$_{1-5}$ alkyl are optionally mono- or polysubstituted with substituents independently selected from halo, OH, O—C$_{1-3}$ alkyl, and C$_{1-3}$ haloalkyl, or R$^p$ and R$^q$, together with the N atom to which they are attached, form a 3-8 membered cycloheteroalkyl group, each optionally substituted with 1, 2, or 3 substituents independently selected from halo and C$_{1-6}$ alkyl;

or any two of R$^6$, R$^7$, R$^8$, R$^9$, and R$^{10}$ or any two of R$^{6'}$, R$^{7'}$, R$^{8'}$, R$^{9'}$, and R$^{10'}$ form a 5- or 6-membered ring;

R$^{11}$ and R$^{11'}$ are independently selected from H, halo, and C$_{1-6}$ alkyl;

B, B', C, and C' are independent selected from C and N$^+$;

n is 0, 1, 2, 3, or 4;

s and t are independently selected from 0, 1, 2, 3, and 4; and

Y$^-$ is the conjugate base of a pharmaceutically suitable organic or inorganic acid.

In some embodiments, n is 1, 2, 3, or 4.
In some embodiments, n is 0.
In some embodiments, the compound of Formula II has Formula III (III)

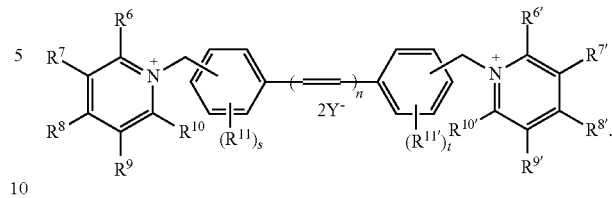

In some embodiments, n is 1, 2, 3, or 4.
In some embodiments, n is 0.
In some embodiments, the compound of Formula II has Formula IV (IV)

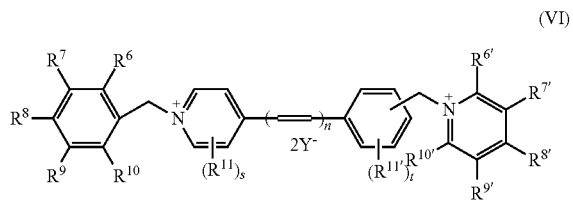

In some embodiments, R$^6$, R$^7$, R$^9$, R$^{10}$, R$^{6'}$, R$^{7'}$, R$^{9'}$, and R$^{10'}$ all are H.

In some embodiments, R$^8$ is NR$^p$R$^q$. In certain embodiments, R$^p$ and R$^q$, together with the N atom to which they are attached, form a 5-7 membered cycloheteroalkyl group.

In other embodiments, R$^p$ and R$^q$, together with the N atom to which they are attached, form a pyrrolidino, piperidino, or perhydroazepino group.

In some embodiments, R$^8$ is N(CH$_3$)$_2$. In other embodiments, R$^8$ is NHR$^q$. In certain embodiments, R$^8$ is NH$_2$.

In some embodiments, R$^{11}$ and R$^{11'}$ both are H.
In other embodiments, n is 2. In some embodiments, n is 3.

In some embodiments, Y$^-$ is Br$^-$.
In some embodiments, the compound of Formula II has Formula VI (VI)

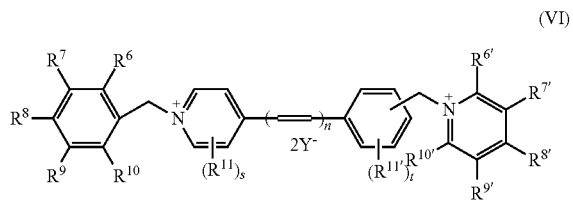

In some embodiments, n is 1, 2, 3, or 4.
In some embodiments, n is 0.
In some embodiments, R$^6$, R$^7$, R$^9$, R$^{10}$, R$^{6'}$, R$^{7'}$, R$^{9'}$, and R$^{10'}$ all are H.

In some embodiments, R$^8$ is NR$^p$R$^q$. In certain embodiments, R$^p$ and R$^q$, together with the N atom to which they are attached, form a 5-7 membered cycloheteroalkyl group. In other embodiments, R$^p$ and R$^q$, together with the N atom to which they are attached, form a pyrrolidino, piperidino, or perhydroazepino group.

In some embodiments, R$^8$ is N(CH$_3$)$_2$. In other embodiments, R$^8$ is NHR$^q$. In certain embodiments, R$^8$ is NH$_2$.

In some embodiments, R$^{8'}$ is NR$^{p'}$R$^{q'}$. In certain embodiments, R$^{p'}$ and R$^{q'}$, together with the N atom to which they are attached, form a 5-7 membered cycloheteroalkyl group. In other embodiments, $R^{p'}$ and $R^{q'}$, together with the N atom to which they are attached, form a pyrrolidino, piperidino, or perhydroazepino group.

In some embodiments, $R^{8'}$ is $N(CH_3)_2$. In other embodiments, $R^{8'}$ is $NHR^q$. In certain embodiments, $R^{8'}$ is $NH_2$.

In some embodiments, $R^{11}$ and $R^{11'}$ are both H.

In other embodiments, n is 2.

In some embodiments, $Y^-$ is $Br^-$.

In some embodiments, the compound of Formula II is

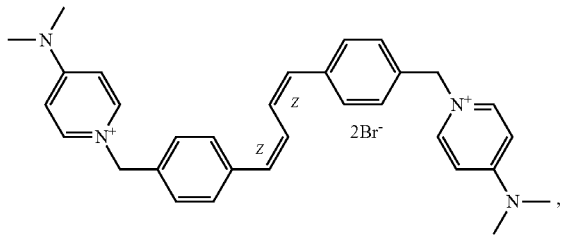

In some embodiments, the compound of Formula II is

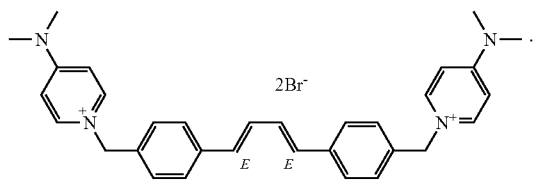

In some embodiments, the compound of Formula II is

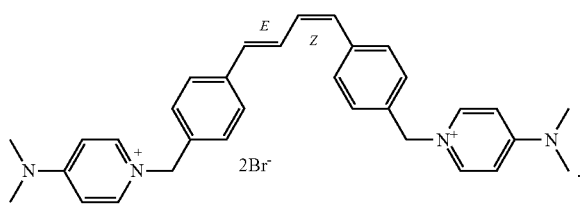

In some embodiments, the compound of Formula II is

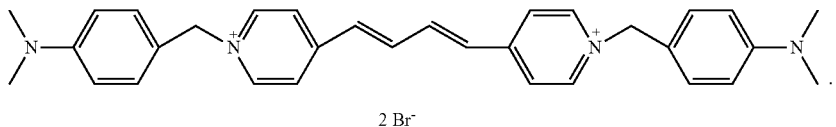

In some embodiments, the compound of Formula II is

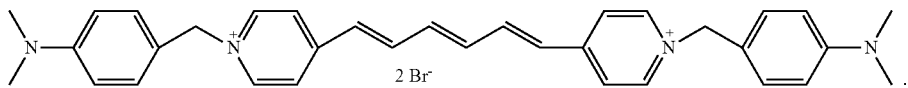

The invention provides methods of diagnosing and/or treating a cancer disease associated with choline kinase (ChoK), the method comprising administering to a subject an effective amount of a composition comprising a compound of Formula V

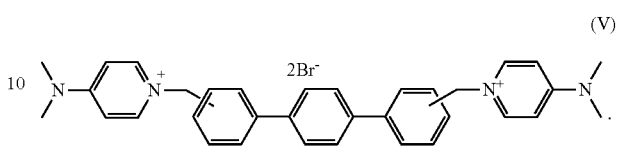

The invention further provides methods for diagnosing and/or treating a cancer disease associated with choline kinase (ChoK), the method comprising: administering to a subject an effective amount of a composition comprising a compound of an intrinsically fluorescent bis-heterocyclic ChoK inhibitor or a bis-heterocyclic ChoK inhibitor such as (1,4-[4-4'-Bis-{[4-(dimethylamine)pyridinium-1-yl]methyl}diphenyl]butane dibromide) (MN58b) operably linked to a fluorescent dye, in which the composition is capable of diagnosing and/or treating cancer diseases associated with ChoK. In some embodiments, the methods include simultaneously diagnosis and treatment of a cancer disease. In some embodiments, the methods include diagnosis only. In one example, the compositions of the invention can report Chok status, but may not elicit a therapeutic response, for example, probes may be tolerable at doses suitable for imaging.

The invention further provides a method for diagnosing a cancer disease associated with choline kinase (ChoK), the method comprising: administering to a subject an effective amount of a composition comprising a compound of Formula I,

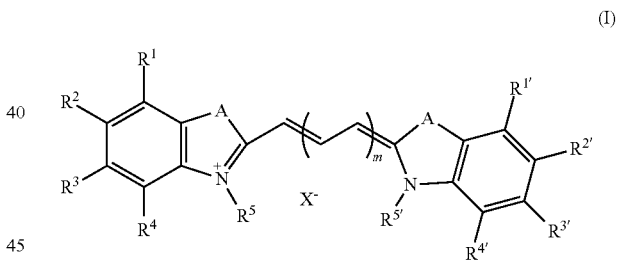

wherein:
$R^1$, $R^2$, $R^3$, $R^4$, $R^{1'}$, $R^{2'}$, $R^{3'}$, and $R^{4'}$ are independently selected from H, halo, $C_{1-6}$ alkyl, $C_{2-6}$ alkenyl, and $C_{1-6}$ haloalkyl, or any two of R¹, R², R³, and R⁴ or any two of R¹', R²', R³', and R⁴' form a 5- or 6-membered ring;

R⁵ and R⁵' are independently selected from $C_{1-6}$ alkyl, $C_{1-6}$ omega-hydroxyalkyl;

m is 1, 2, 3, 4, or 5;

A is O, S, or $C(CH_3)_2$; and

X⁻ is the conjugate base of a pharmaceutically suitable organic or inorganic acid.

The invention further provides a method for treating a cancer disease associated with choline kinase (ChoK), the method comprising: administering to a subject an effective amount of a composition comprising a compound of Formula I,

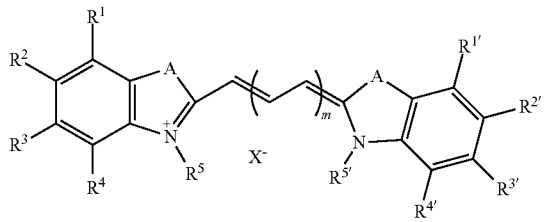

(I)

wherein:

R¹, R², R³, R⁴, R¹', R²', R³', and R⁴' are independently selected from H, halo, $C_{1-6}$ alkyl, $C_{2-6}$ alkenyl, and $C_{1-6}$ haloalkyl, or any two of R¹, R², R³, and R⁴ or any two of R¹', R²', R³', and R⁴' form a 5- or 6-membered ring;

R⁵ and R⁵' are independently selected from $C_{1-6}$ alkyl, $C_{1-6}$ omega-hydroxyalkyl;

m is 1, 2, 3, 4, or 5;

A is O, S, or $C(CH_3)_2$; and

X⁻ is the conjugate base of a pharmaceutically suitable organic or inorganic acid.

The invention further provides a method for diagnosing a cancer disease associated with choline kinase (ChoK), the method comprising: administering to a subject an effective amount of a composition comprising a compound of Formula II,

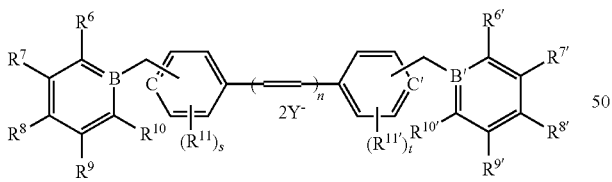

(II)

wherein:

R⁶, R⁷, R⁸, R⁹, R¹⁰, R⁶', R⁷', R⁸', R⁹', and R¹⁰' are independently selected from H, halo, $C_{1-6}$ alkyl, $C_{2-6}$ alkenyl, $C_{1-6}$ haloalkyl, and $NR^pR^q$, wherein $R^p$ and $R^q$ are independently selected from H, $C_{1-8}$ alkyl, $C_{3-6}$ cycloalkyl, aryl, heteroaryl, aryl-$C_{1-5}$ alkyl, and heteroaryl-$C_{1-5}$ alkyl, wherein said $C_{1-8}$ alkyl, $C_{3-6}$ cycloalkyl, aryl, heteroaryl, aryl-$C_{1-5}$ alkyl, and heteroaryl-$C_{1-5}$ alkyl are optionally mono- or polysubstituted with substituents independently selected from halo, OH, O—$C_{1-3}$ alkyl, and $C_{1-3}$ haloalkyl, or $R^p$ and $R^q$, together with the N atom to which they are attached, form a 3-8 membered cycloheteroalkyl group, each optionally substituted with 1, 2, or 3 substituents independently selected from halo and $C_{1-6}$ alkyl;

or any two of R⁶, R⁷, R⁸, R⁹, and R¹⁰ or any two of R⁶', R⁷', R⁸', R⁹', and R¹⁰' form a 5- or 6-membered ring;

R¹¹ and R¹¹' are independently selected from H, halo, and $C_{1-6}$ alkyl;

B, B', C, and C' are independent selected from C and N⁺;

n is 0, 1, 2, 3, or 4;

s and t are independently selected from 0, 1, 2, 3, and 4; and

Y⁻ is the conjugate base of a pharmaceutically suitable organic or inorganic acid.

In some embodiments, n is 1, 2, 3, or 4.

In some embodiments, n is 0.

The invention further provides a method for diagnosing a cancer disease associated with choline kinase (ChoK), the method comprising administering to a subject an effective amount of a composition comprising a compound of Formula V,

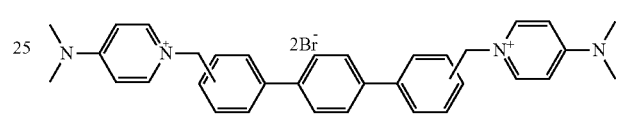

(V)

The invention further provides a method for treating a cancer disease associated with choline kinase (ChoK), the method comprising: administering to a subject an effective amount of a composition comprising a compound of Formula II,

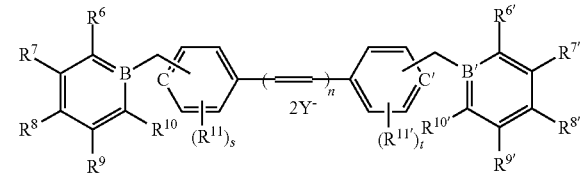

(II)

wherein:

R⁶, R⁷, R⁸, R⁹, R¹⁰, R⁶', R⁷', R⁸', R⁹', and R¹⁰' are independently selected from H, halo, $C_{1-6}$ alkyl, $C_{2-6}$ alkenyl, $C_{1-6}$ haloalkyl, and $NR^pR^q$, wherein $R^p$ and $R^q$ are independently selected from H, $C_{1-8}$ alkyl, $C_{3-6}$ cycloalkyl, aryl, heteroaryl, aryl-$C_{1-5}$ alkyl, and heteroaryl-$C_{1-5}$ alkyl, wherein said $C_{1-8}$ alkyl, $C_{3-6}$ cycloalkyl, aryl, heteroaryl, aryl-$C_{1-5}$ alkyl, and heteroaryl-$C_{1-5}$ alkyl are optionally mono- or polysubstituted with substituents independently selected from halo, OH, O—$C_{1-3}$ alkyl, and $C_{1-3}$ haloalkyl, or $R^p$ and $R^q$, together with the N atom to which they are attached, form a 3-8 membered cycloheteroalkyl group, each optionally substituted with 1, 2, or 3 substituents independently selected from halo and $C_{1-6}$ alkyl;

or any two of R⁶, R⁷, R⁸, R⁹, and R¹⁰ or any two of R⁶', R⁷', R⁸', R⁹', and R¹⁰' form a 5- or 6-membered ring;

R¹¹ and R¹¹' are independently selected from H, halo, and $C_{1-6}$ alkyl;

B, B', C, and C' are independent selected from C and N⁺;

n is 0, 1, 2, 3, or 4;

s and t are independently selected from 0, 1, 2, 3, and 4; and

Y⁻ is the conjugate base of a pharmaceutically suitable organic or inorganic acid.

In some embodiments, n is 1, 2, 3, or 4.

In some embodiments, n is 0.

The invention further provides a method for treating a cancer disease associated with choline kinase (ChoK), the method comprising administering to a subject an effective amount of a composition comprising a compound of Formula V,

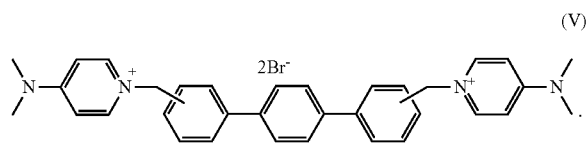

(V)

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

In some embodiments, the method includes detecting the fluorescence in the subject by an imaging device. Examples of imaging methods include, but are not limited to, spectroscopy and near infrared imaging (NIR). In a particular embodiment, the level of choline kinase is measured non-invasively in vivo by a fluorescence within the NIR range (e.g., excitation 640-850 nm, emission 700-900 nm). In other embodiments, the fluorescence can be measured ex vivo. In other embodiments, the fluorescence can be measured in vitro.

Examples of cancers/tumors which may be diagnosed and/or treated include breast cancer (including HER2+, Her2/neu+, triple negative, and metastatic), a lung cancer, a bladder cancer, a prostate cancer, a colorectal cancer, an ovarian cancer, a gastrointestinal cancer, or any cancer associated with the ChoK mediated signaling. Examples of a lung cancer include, but are not limited to a small cell lung cancer (SCLC) or a non-small cell lung cancer (NSCLC).

Cancers that express or overexpress or are associated with the expression or overexpression of ChoK may be diagnosed and/or treated by the invention. However, cancer to be treated by the combination therapy herein may be any cancer, not simply those that express or overexpress ChoK.

Cancers to be diagnosed and/or treated include primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory (e.g., androgen-independent prostate cancer; or hormone-refractory breast cancer, such as breast cancer that is refractory to tamoxifen); those that are refractory to treatment with one or more chemotherapeutic agents; those that are refractory to radiation; and those that are refractory to combinations of chemotherapy and radiation, chemotherapy and hormone therapy, or hormone therapy and radiation.

Therapy may be "first-line", i.e., as an initial treatment in patients who have had no prior anti-cancer treatments, either alone or in combination with other treatments; or "second-line", as a treatment in patients who have had one prior anti-cancer treatment regimen, either alone or in combination with other treatments; or as "third-line," "fourth-line," etc. treatments, either alone or in combination with other treatments.

Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of tumor.

Cancers that may be diagnosed or treated include tumors that are not vascularized, or not yet substantially vascularized, as well as vascularized tumors. The cancers may be comprised of non-solid tumors (such as leukemias and lymphomas) or may be solid tumors. Types of cancers to be treated with the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are included.

In some embodiments, provided herein is a pharmaceutical composition comprising an intrinsically fluorescent choline kinase (ChoK) inhibitor (e.g., an intrinsically fluorescent bis-heterocyclic ChoK inhibitor).

In another embodiment, provided herein is a pharmaceutical composition comprising a choline kinase (ChoK) inhibitor (e.g., a bis-heterocyclic ChoK inhibitor) operably linked to a fluorescent dye.

The invention also provides a pharmaceutical composition comprising small molecule conjugate or other agents of this invention and one or more pharmaceutically acceptable carriers. "Pharmaceutically acceptable carriers" include any excipient which is nontoxic to the cell or mammal being exposed thereto at the dosages and concentrations employed. The pharmaceutical composition may include one or additional therapeutic agents.

Pharmaceutically acceptable carriers include solvents, dispersion media, buffers, coatings, antibacterial and antifungal agents, wetting agents, preservatives, buffers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

The pharmaceutical compositions of the invention may be formulated in a variety of ways, including for example, solid, semi-solid (e.g., cream, ointment, and gel), and liquid dosage forms, such as liquid solutions (e.g., topical lotion or spray), dispersions or suspensions, tablets, pills, powders, liposomes, micelles, nanopariticles and suppositories. In some embodiments, the compositions are in the form of injectable or infusible solutions. The composition is in a form suitable for oral, intravenous, intraarterial, intramuscular, subcutaneous, parenteral, transmucosal, transdermal, or topical administration. The composition may be formulated as an immediate, controlled, extended or delayed release composition.

More particularly, pharmaceutical compositions suitable for use include sterile aqueous solutions (where water soluble) or dispersions and sterile powders for the extemporaneous preparation of sterile solutions or dispersions. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

In some embodiments, the composition includes isotonic agents, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

Sterile solutions can be prepared by incorporating the molecule, by itself or in combination with other active agents, in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. Patent Application Publication No. 2002/0102208 A1, which is incorporated herein by reference in its entirety.

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals (e.g., domestic animals) can also be treated. Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

The invention further provides a kit comprising a diagnostically or therapeutically effective amount of a composition of the invention.

The composition may be administered alone, or in combination with one or more other therapeutically effective agents. The other therapeutically effective agent may be conjugated to or otherwise incorporated into the same composition as ChoK inhibitor, or may be administered as a separate composition. The other therapeutic agent or treatment may be administered prior to, during and/or after the administration of the composition.

The administration of the composition with other agents and/or treatments may occur simultaneously, or separately, via the same or different route, at the same or different times. Dosage regimens may be adjusted to provide the optimum desired response (e.g., a therapeutic or prophylactic response).

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, oral (for example, in capsules, suspensions or tablets), parenteral (including subcutaneous, intravenous, intramedullary, intraarticular, intramuscular, or intraperitoneal injection), rectal, topical, and transdermal. Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

The term "ChoK" as used herein may refer to any isoform of ChoK. Examples of ChoK may include, but are not limited to, ChoK-alpha 1, ChoK-alpha2, and ChoK beta.

The term "subject," as used herein, may refer to any mammal, for example, a human or an animal (e.g., domestic animal).

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

EXAMPLES

Example 1

Synthesis of Choline Kinase Inhibitors and Imaging Agents

Our first task is to synthesize MN58b, the most effective known competitive inhibitor of choline kinase, which was not commercially available. The next step was to synthesize a mixed conjugate linking hemicholinium-3 or MN58b to the near infrared fluorophore, pyropheophorbide a.

I. Synthesis of MN-58b, 1,1'-[Butane-1,4-diylbis (benzene-1,4-diylmethylene)]-bis[(4-dimethylamino) pyridinium]dibromide 1. Preparation of 1,4-bis(4-bromomethylphenyl)butane 1,4-Diphenylbutane (2 g, 9.51 mmol) was added to a mixture of 48% aqueous HBr (4.15 mL, 39.9 mmol) and glacial AcOH (50 mL), followed by 1,3,5-trioxane (0.57 g, 6.34 mmol) and hexadecyltrimethylammonium bromide (52 mg, 0.143 mmol). The mixture was then well stirred such that only a single layer could be seen then heated to a gentle reflux for 8 h. Then, the volatiles were removed under reduced pressure. The product was isolated by column chromatography (silica gel, hexane/benzene 1/1, v/v). Isolated 1,4-bis(4-bromomethylphenyl)butane (1.959 g, yield 52%) was a white solid, m.p. 119-121° C. (from acetone). $^1$H NMR (500 MHz, CDCl$_3$, δ ppm) 7.04 ppm (AB, A=7.18, B=6.89, J$_{AB}$=9 Hz, 8H), 4.53 (s, 4H), 2.66 (m, 4H), 1.62 (m, 4H).

2. Synthesis of MN-58b, 1,1'-[Butane-1,4-diylbis (benzene-1,4-diylmethylene)]-bis[(4-dimethylamino) pyridinium]dibromide The mixture of 4-dimetylaminopyridine (238.0 mg, 1.948 mmol) and 1,4-bis(4 bromomethylphenyl)butane (385.9 mg, 0.974 mmol) in dry ethanol (30 mL) was heated and stirred at 160° C. in a 45 mL Parr autoclave equipped with a magnetic stirring bar for 3 h. The white solid product was precipitated twice from EtOH into Et$_2$O, dissolved in deionized water and lyophilized Yield: 96%, mp 98-100° C. (from water). $^1$H NMR (300 MHz, DMSO-d$_6$, δ ppm): 8.32 (d, J=7.9 Hz, 4H, H-2pyr), 7.39 (d, J=8.2 Hz, 4H, Ph), 7.31 (d, J=8.2 Hz, 4H, Ph), 7.09 (d, J=7.9 Hz, 4H, H-3pyr), 5.42 (s, 4H, CH$_2$N$^+$), 3.33 (s, 12H, NMe$_2$), 2.72 (t, 4H, CH$_2$Ph), 1.70 (q, 4H, C—CH$_2$—C).

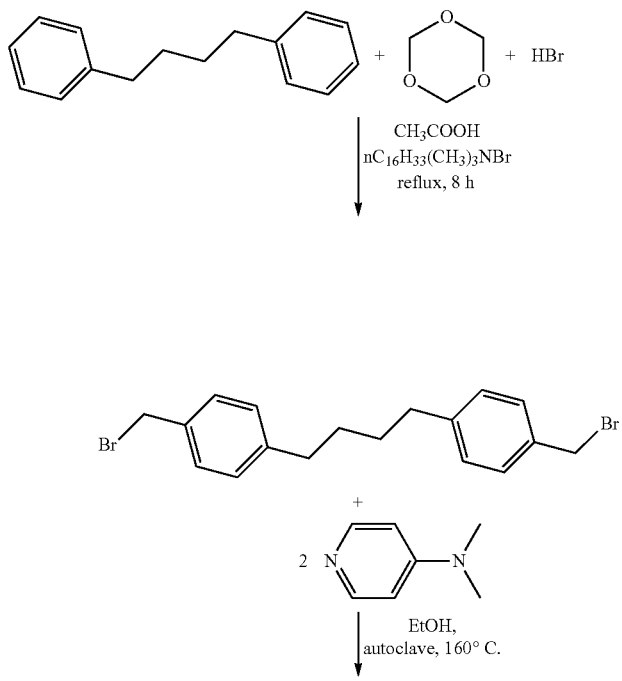

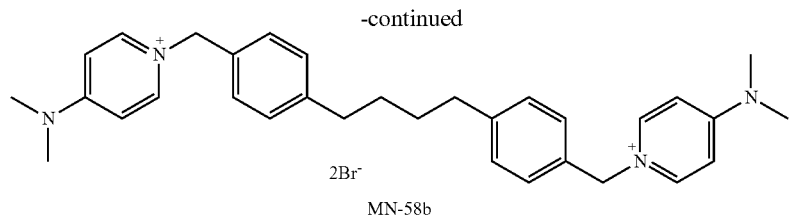

MN-58b

II. Synthesis of PyropheophorbideC$_{12}$-HC-3 conjugate

1. Preparation of PyropheophorbideC$_{12}$ acid and its coupling with HC-3: Synthesis of PyropheophorbideC$_{12}$ acid (λ-Pyropheophorbideamidolauric acid or 17$^3$-deoxy-17$^3$-(α-carbhydroxyundecylene-λ-amino)pyropheophorbide a)

A 200 mL round bottom flask was charged with pyropheophorbide acid (207 mg, 0.38 mmol), NHS (43.9 mg, 0.38 mmol), EDC (73.14 mg, 0.38 mmol), DMAP (23.3 mg, 0.19 mmol) and 200 ml of dry DCM. The reaction mixture was stirred in dark under Ar for 3 h until pyropheophorbide acid was converted completely into its SU ester (TLC CHCl$_3$/MeOH=5/1). Then H$_2$N(CH$_2$)$_{11}$CO$_2$H (82.15 mg, 0.38 mmol) and dry pyridine (25 ml) were added. The second reaction was carried out for 48 h until complete conversion of Pyro-SU. After solvents were evaporated, the solid residue was dissolved in 100 mL of DCM, rinsed twice with 2% HCl, then water. The product was isolated by column chromatography on silica gel (DCM-ethyl acetate, DCM-ethyl acetate-MeOH, ethyl acetate-MeOH). Isolated yield 47%. $^1$H NMR (360 MHz, CDCl$_3$, δ ppm): 10.11 ppm (s, 1H, 17$^4$-C(O)NH); 9.18 (s, 1H, 10-H); 9.06 (s, 1H, 5-H); 8.41 (s, 1H, 20-H); 7.78 (dd, J=11.7 Hz, J=18 Hz, 1H, 3$^1$-CH=CH$_2$); 6.12 (d, J=18 Hz, 1H, trans-3$^2$-CH=CHH); 6.03 (d, J=11.7 Hz, 1H, cis-3$^2$-CH=CHH); 5.06 (AB, A=5.14, B=4.99, J$_{AB}$=20.2 Hz, 2H, 13$^2$-CH$_2$); 4.36 (qd, J=7.6 Hz, J=1.8 Hz, 1H, 18-H); 4.16 (dm, 8.6 Hz, 1H, 17-H), 3.47 (s, 3H, 2$^1$-CH$_3$); 3.42 (q, 7.6 Hz, 2H, 8$^1$-CH$_2$CH$_3$); 3.26 (s, 3H, 12$^1$-CH$_3$); 3.1 (m, 2H, 17$^5$-NHCH$_2$CH$_2$—); 2.98 (s, 3H, 7$^1$-CH$_3$); 2.63-2.44 (m, 4H, 17$^2$ and 17$^{15}$2×-CH$_2$C(O)), 2.26-2.12 (m, 4H, 17$^1$ and 17$^{14}$ 2×-CH$_2$CH$_2$C(O)); 1.72 (d, J=7.6 Hz, 3H, 18$^1$-CH$_3$CH), 1.52 (t, J=7.6 Hz, 3H, 8$^2$-CH$_2$CH$_3$), 1.50-1.15 (m, 16H, 17$^{6-13}$ 8×CH$_2$); −1.78 (s, 2H, A and C2×NH). MALDI-TOF, m/z: (M+Na)$^+$ 754.51, calculated for C$_{45}$H$_{57}$N$_5$NaO$_4$ 754.43.

2. Coupling of PyropheophorbideC$_{12}$ acid and HC-3

PyropheophorbideC$_{12}$ acid (78 mg, 0.12 mmol) HC-3 (122 mg, 0.21 mmol), EDC (203 mg, 1.1 mmol), DMAP (13.1 mg, 0.11 mmol) and 250 ml of dry DMF were mixed in 500 mL flask. The reaction mixture was stirred in dark under Ar for 10 days. The methods can be modified, if needed.

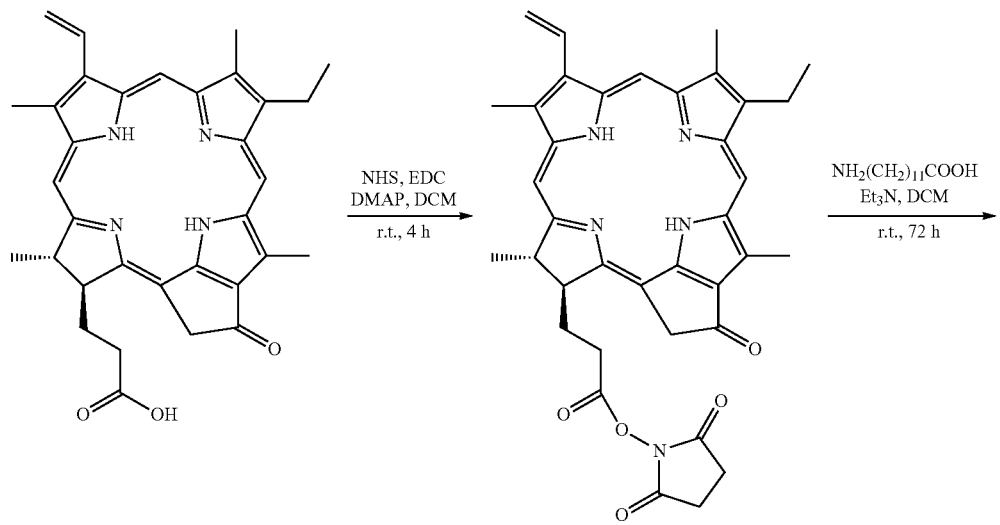

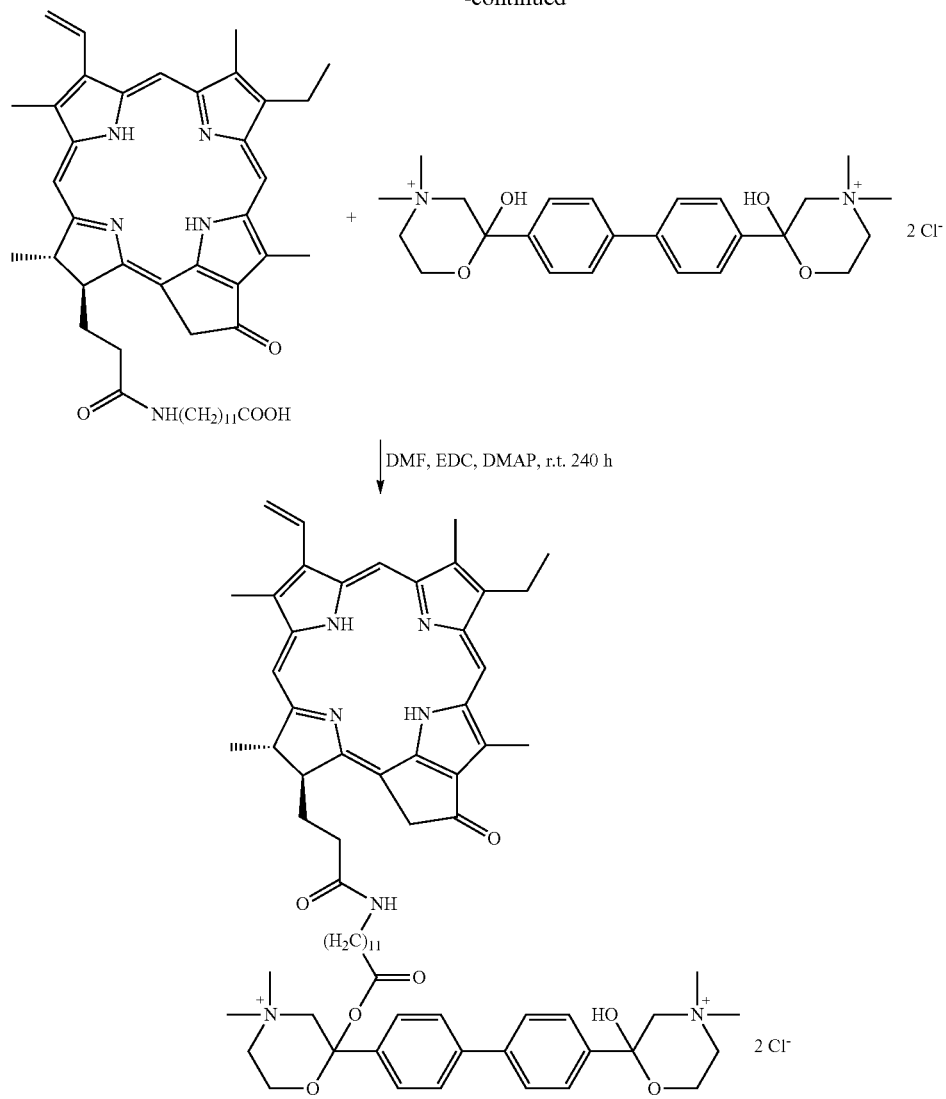

Example 2

Multimodality Imaging of Choline Kinase Activity as a Predictor of Breast Cancer Progression The relative degree of choline uptake and activation can be measured in breast cancer cells and solid tumor xenografts by determining the changes in magnetic resonance (MR)-visible lipid metabolite levels together with measuring fluorescence uptake using near infrared (NIR) choline analogs. One skilled in the art can compare and validate the MR spectroscopy (MRS) with results obtained using NIR optical imaging in breast cancer tumor models where phospholipid metabolite levels are known. Since elevated choline levels are observed in the majority of breast cancers, detecting choline metabolic changes using a dual modality MR and optical imaging approach will provide specific information that may be useful for the diagnosis or staging of breast tumors or monitoring the response to therapy.

Design and Synthesis of Fluorescent Choline Analogs.

Three strategies can be employed for the design and synthesis of fluorescent choline analogs: i) Synthesis of hybrid molecules containing both the known ChoK-inhibiting and fluorescent groups, ii) Modification of the known ChoK inhibitors HC-3 and MN58b to incorporate a fluorescing moiety, and iii) modification of Cy dyes to maximize their ChoK-inhibiting efficiency. The compounds JAS239 and JAS240 are examples of the latter approach.

Synthesis of JAS239 (1-(2-hydroxyethyl)-2-((1E, 3E,5E)-7-4Z/E)-1-(2-hydroxyethyl)-3,3-dimethylindolin-2-ylidene)hepta-1,3,5-trien-1-yl)-3,3-dimethyl-3H-indol-1-ium chloride)

1. Synthesis of 1-(2-hydroxyethyl)-2,3,3-trimethyl-3H-indol-1-ium chloride

The mixture of 2,3,3-trimethyl-3H-indole (1592.3 mg, 10 mmol) and 2-chloroethan-1-ol (1610.2 mg, 20 mmol) in dry ethanol (15 mL) was heated and stirred at 160° C. in a 45 mL Parr autoclave equipped with a magnetic stirring bar for 4 h. The pink solid product was precipitated twice from EtOH with Et$_2$O. Yield 86%. $^1$H NMR (360 MHz, CD$_3$OD, δ ppm): 7.88 ppm (m, 1H); 7.77 (m, 1H); 7.65 (m, 2H); 4.68 (m, 2H); 4.06 (m, 2H); 1.63 (s, 6H); labile OH and N=C—CH$_3$ protons are in exchange with CD$_3$OD. MALDI-TOF, m/z: (M-Cl)$^+$204.35, calculated for C$_{13}$H$_{18}$NO 204.14.

2. Preparation of N-phenyl-N-((1E,3E,5Z)-5-(phenylimino)penta-1,3-dien-1-yl)acetamide and its condensation with 1-(2-hydroxyethyl)-2,3,3-trimethyl-3H-indol-1-ium chloride A solution of acetic anhydride (112.3 mg, 1.1 mmol) in CH$_2$Cl$_2$ (2 mL) was added to a cooled (−20° C.), stirred suspension of N-((1E,3E,5Z)-5-(phenylimino)penta-1,3-dien-1-yl) benzenaminium chloride (142.4 mg, 0.5 mmol) and triethylamine (222.6 mg, 2.2 mmol) in CH$_2$Cl$_2$ (10 mL). The resulting clear solution was stirred for another 3 h at r.t. and concentrated under high vacuum. The residue containing N-phenyl-N-((1E,3E,5Z)-5-(phenylimino)penta-1,3-dien-1-yl)acetamide was dissolved in ethanol (5.0 mL) and added dropwise to a refluxing solution of 1-(2-hydroxyethyl)-2,3,3-trimethyl-3H-indol-1-ium chloride (360.0 mg, 1.5 mmol) and anhydrous sodium acetate (200 mg, 2.5 mmol) in ethanol (100 mL). The mixture was refluxed for 5 h and concentrated. The product JAS 239 (1-(2-hydroxyethyl)-2-((1E,3E,5E)-7-((Z1E)-1-(2-hydroxyethyl)-3,3-dimethylindolin-2-ylidene)hepta-1,3,5-trien-1-yl)-3,3-dimethyl-3H-indol-1-ium chloride) was isolated by column chromatography (silica gel, ethyl acetate-methanol (0→100%)). Yield 19.9%. $^1$H NMR (360 MHz, CD$_3$OD, δ ppm): 7.93 (t (dd), J=13.1 Hz, 2H); 7.58 (t (dd), J=12.8 Hz, 1H); 7.46 (d, J=7.2 Hz, 2H); 7.38 (td, J=7.4 Hz, J=1.1 Hz, 2H); 7.29 (d, J=7.9 Hz, 2H); 7.23 (td, J=7.2 Hz, J=0.7 Hz, 2H); 6.53 (t (dd), J=12.6 Hz, 2H); 6.35 (d, J=13.7 Hz, 2H); 4.21 (t, J=5.8 Hz, 4H); 4.92 (t, J=5.8 Hz, 4H); 1.70 (s, 12H). MALDI-TOF, m/z: (M-Cl)$^+$ 469.56, calculated for C$_{31}$H$_{37}$N$_2$O$_2$ 469.28.

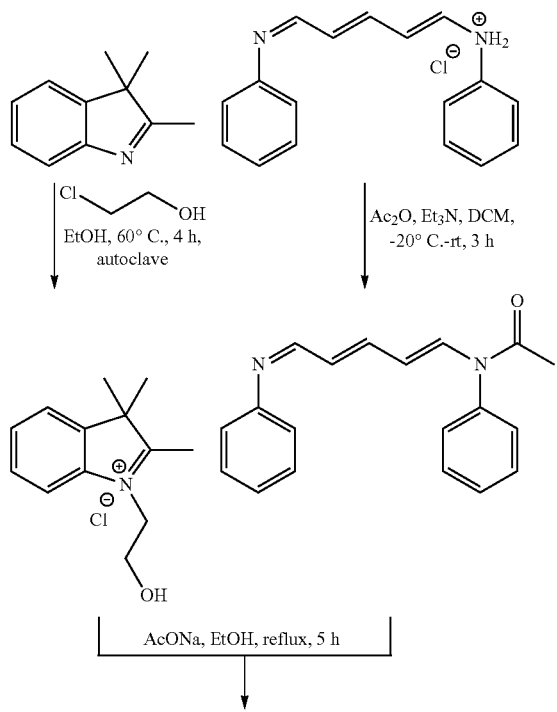

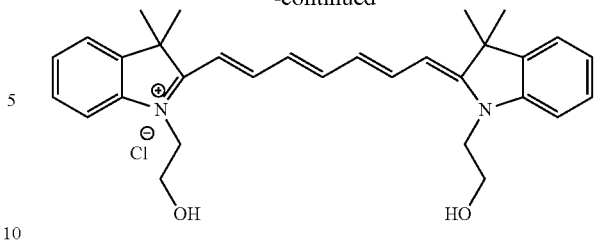

Molecules can be synthesized, based on combinations of the near-infrared dyes pyropheophorbide a and Cy 7 and on the choline antagonists HC-3 and MN58b. These can be of the type where the NIR dye is conjugated to HC-3 or MN58b. Variations on these molecules can be produced by varying the site of attachment and length of the linker molecule.

Synthesis of Asymmetric Four-Methine Disalts

The synthesis of an asymmetric four-methine disalt is shown below. Para-methyl cinnamaldehyde is brominated via a radical mechanism by NBS (a). The product benzylates DMAP to produce an MN58b-like-substituted acrolein (b). This aldehyde salt is coupled with N-alkyl benzothiazolium, benzoxazolium or 2,3,3-timethyl-2H-indolium salts. This coupling is undertaken with piperidine in AcOH (c). The resulting mixed halide is treated with an excess of iodide and recrystallized (d). To produce the methine-linked conjugate a Horner-Emmons-Wadsworth coupling is employed. To do this the starting "benzazolium" salts is dehydrohalogenated with alkali in water-EtOH (e) resulting in 2,3-dihydro-3-alkyl-2-methylenebenzothiazole, 2,3-dihydro-3-alkyl-2-methylenebenzoxazole and 1-alkyl-3,3-dimethyl-2-methyleneindoline. These three compounds will by formylated using the Vilsmeier reaction (POCl$_3$, DMF followed by basic hydrolysis (f). The phosphonate counterpart is synthesized by an Arbuzov reaction between p-xylyl bromide and triethyl phosphite (g). The coupling of the aldehydes and the phosphonates is carried out with tBuOK in DMF (h). If necessary the hydroxyethyl group (Y=CH$_2$OH) will be protected (e.g. with dihydropyran,) and deprotected after the coupling. The NBS radical bromination (i) incorporates Br into the benzyl position. The last step represents benzylation of DMAP (j) giving the target compound. Variations on these molecules can be produced by varying the site of attachment and length of the linker molecule.

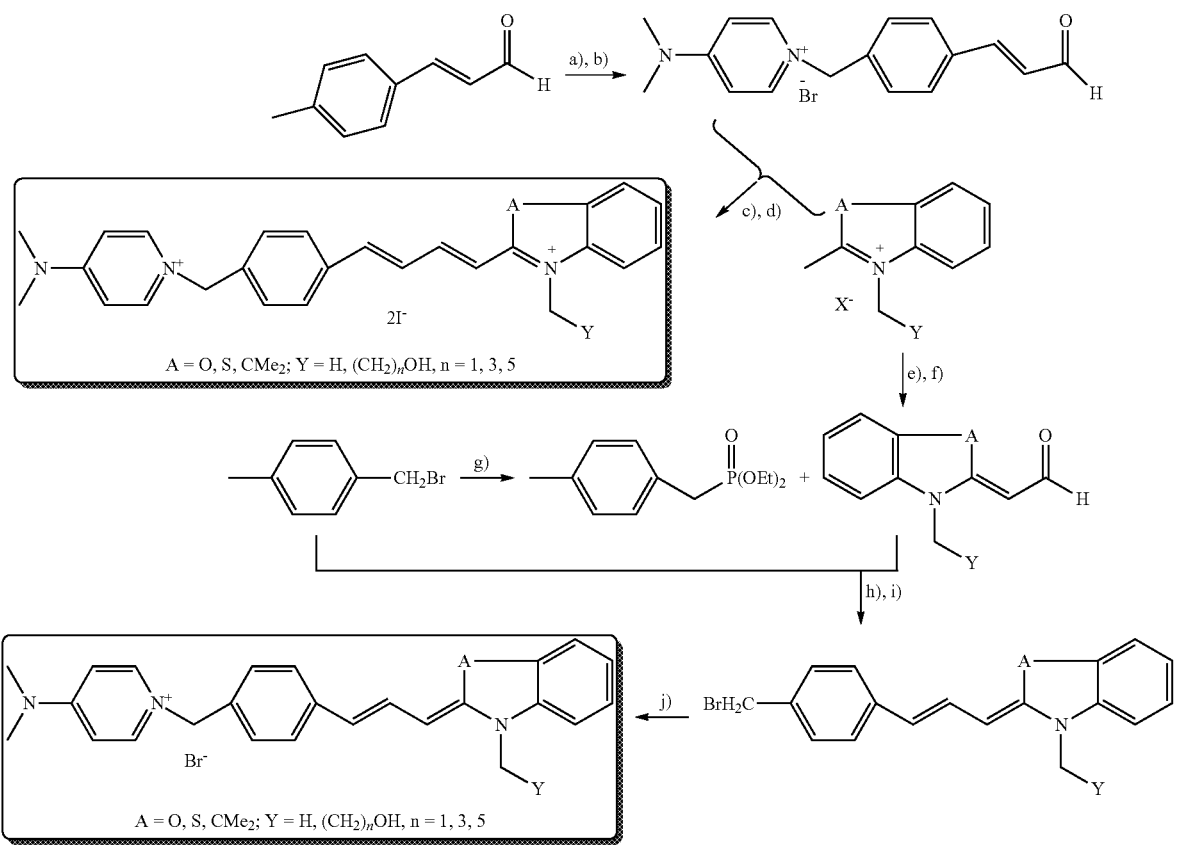

In Vitro Characterization of the Synthesized Probes

The efficacy of the NIR choline analog probes can be examined. This includes determination of fluorescence characteristics and probe solubility followed by measurement of cellular uptake, probe toxicity and the kinetics of choline transport and ChoK inhibition in cells. One skilled in the art can use a series of breast cancer cell lines that display increasing choline levels that correlate with their degree of aggressiveness: MCF-12A, SKBR3, MCF-7, MDA-MB-231 and MDA-MB-435. Quantitative assessment of probe uptake and ChoK inhibition can be performed using fluorimetry and flow cytometry and $^{14}C$ labeled choline uptake along with qualitative information from fluorescence confocal microscopy to assess uptake specificity, subcellular probe location and in situ enzyme kinetic inhibition. These data can be compared with MR spectra of perfused cells and their corresponding homogenates to correlate PC and tCho levels with probe uptake.

In Vivo Detection of Choline Transport and Phosphorylation Using Dual Modality $^{31}P$ and $^{1}H$ MRS and Optical Imaging.

The breast cancer xenografts MDA-MB-231 and MCF-7 can be employed. The experimental protocol consists of MR imaging and spectroscopy ($^{1}H$ and $^{31}P$) to measure native choline levels followed by i.v. injection with fluorophore and NIR optical imaging. Mice will be imaged with NW optical imaging from 0-72 h, with additional MR examinations to determine the effects of the accumulation of NIR choline analogs on phospholipid metabolite levels. At the end of the experiment, mice will be sacrificed and the organs harvested and scanned and/or extracted and analyzed using HPLC MALDI-TOF mass spec. Probes that cause significant changes in in vivo choline metabolites, or display potential as anticancer agents (e g inhibit ChoK in vitro) may be used for further testing. These agents can be injected at higher concentrations and the effects on tumor growth determined. If substantial tumor growth delay is observed, then the imaging experiments may be repeated at these higher concentrations.

Example 3

NIR-Fluorescent Choline Kinase Inhibitors for Cancer Imaging and Therapy

Upregulation of Choline Kinase (ChoK) has been correlated with histological tumor grade and resistance to anti-estrogen therapies in breast cancer, ultimately indicating a poorer prognosis. ChoK catalyzes the conversion of choline to phosphocholine (PC), an important mitogenic second messenger and the first step in biosynthesis of the major membrane phospholipid phosphatidylcholine. Using magnetic resonance spectroscopy, it is difficult to measure the contribution of ChoK to the elevated PC peak observed during tumor progression and the depletion of PC corresponding to treatment response. This is due to the competing actions of phospholipases and difficulties in resolving the individual choline-containing metabolites in vivo. Analogs of the bis-heterocyclic choline mimetic Hemicholinium-3, such as MN58b and TCD-717, have previously been identified as specific ChoK inhibitors. We have synthesized a series of fluorescent polymethine dyes that incorporate the features essential for effective inhibition: bis-heterocyclic structure which may be symmetric or non-symmetric, quaternary ammonium groups, water solubility, and an aliphatic spacer of optimized length. We have also synthesized the most extensively studied ChoK inhibitor, MN58b, as a positive control. Fluorescent within the NIR range (excitation 640-745 nm, emission 770 nm), the dyes are suitable for detection of ChoK expression in vivo. The ability to measure ChoK non-invasively would provide complementary information to the metabolic assessment provided by MRS.

We identified two prototype compounds, JAS239 and JAS240, which inhibit ChoK with IC50s comparable to MN58b. ChoK activity was assessed in triple-negative MDA-MB-231 breast cancer cells and in non-transformed MCF10a breast epithelial cells using $^{14}$C-labeled choline uptake. The metastatic MDA-MB-231 cancer line displayed a greater sensitivity to JAS239 than non-transformed MCF10a breast epithelial cells. Confocal microscopy confirmed the probes were localized to the cytosol where ChoK is active, and excluded from the nucleus where DNA intercalation could cause non-specific cytotoxicity or mutagenesis. Fluorimetry studies showed that JAS239 uptake was linearly proportional to concentration and independent of exogenous choline concentration, indicating that uptake does not rely on choline transporters. Addition of exogenous choline reverses ChoK inhibition, signifying competitive inhibition at the choline-binding site. Cell uptake is detectable within 15 min and ChoK inhibition present by 60 min. These data demonstrate that this strategy works for optical detection of ChoK expression. This method could be employed for breast cancer staging and assessment of therapy response.

Figure 2:
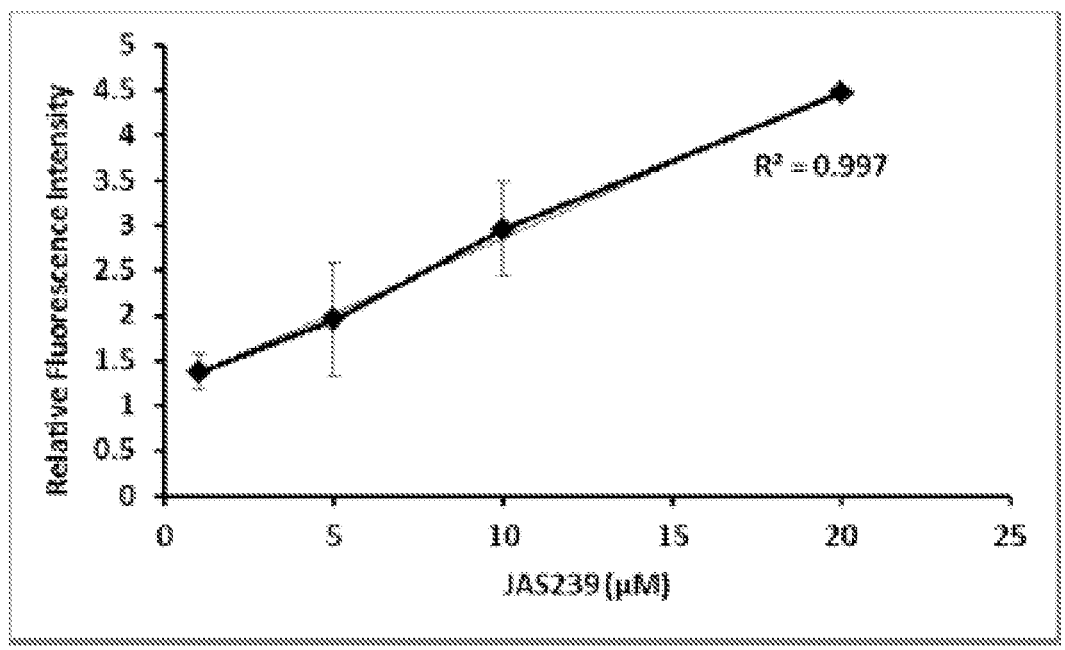
FIG. 2 illustrates that fluorescence intensity is linearly proportional to JAS239 concentration added in vitro. MDA-MB-231 cells were incubated with JAS239 and the fluorescence measured (Excitation 640 nm, Emission 770 nm).

FIG. 1 shows absorption and emission spectra of JAS239 and JAS240 in ethanol at room temperature, demonstrating fluorescence in the NIR range. As shown in FIG. 2, fluorescence intensity is linearly proportional to JAS239 concentration added in vitro. MDA-MB-231 cells were incubated with JAS239 and the fluorescence measured (Excitation 640 nm, Emission 770 nm).

Figure 3:
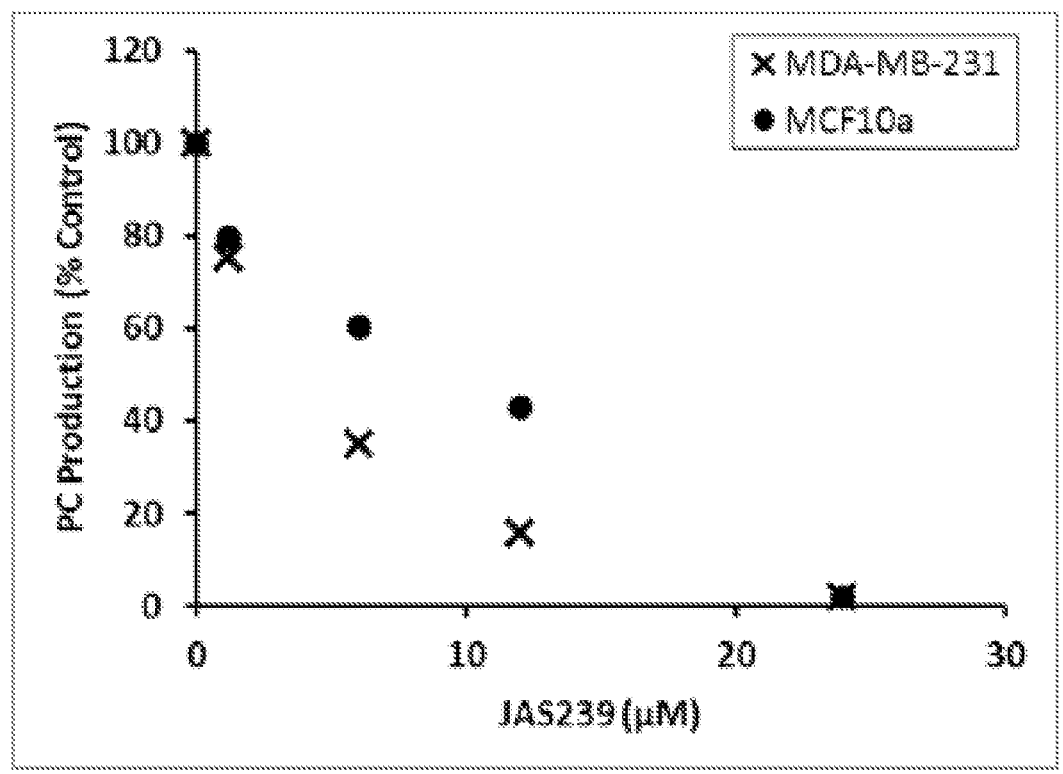
FIG. 3 depicts that malignant breast cell lines are more sensitive to JAS239. MDA-MB-231 cells and non-malignant MCF-10a cells were incubated for 14 hr with JAS239 and analyzed by TLC/autoradiography after $^{14}$C-choline labeling.

FIG. 3 shows that malignant breast cell lines are more sensitive to JAS239. MDA-MB-231 cells and non-malignant MCF-10a cells were incubated for 14 hr with JAS239 and analyzed by TLC/autoradiography after $^{14}$C-choline labeling.

Figure 4:
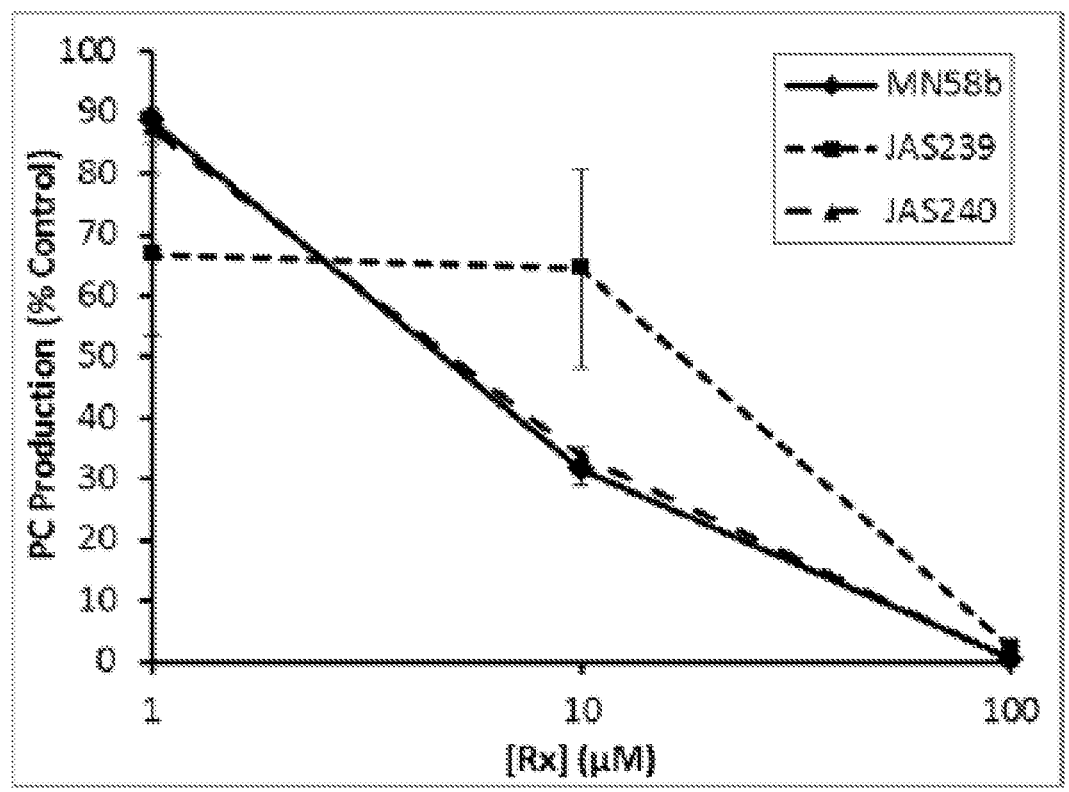
FIG. 4 depicts inhibition of ChoK by novel NIR-fluorescent dyes. MDA-MB-231 cells were incubated with increasing concentrations of JAS239 or JAS240. 14 h following $^{14}$C-choline addition, cells were extracted for TLC/autoradiography analysis. The dyes demonstrate ChoK inhibition at physiologically-relevant concentrations. MN58b was used as positive control. These data represent PC production as % control+standard deviation for three separate experiments.

FIG. 4 demonstrates inhibition of ChoK by novel NIR-fluorescent dyes. MDA-MB-231 cells were incubated with increasing concentrations of JAS239 or JAS240. 14 h following $^{14}$C-choline addition, cells were extracted for TLC/autoradiography analysis. The dyes demonstrate ChoK inhibition at physiologically-relevant concentrations. MN58b was used as positive control. These data represent PC production as % control+standard deviation for three separate experiments.

Figure 5:
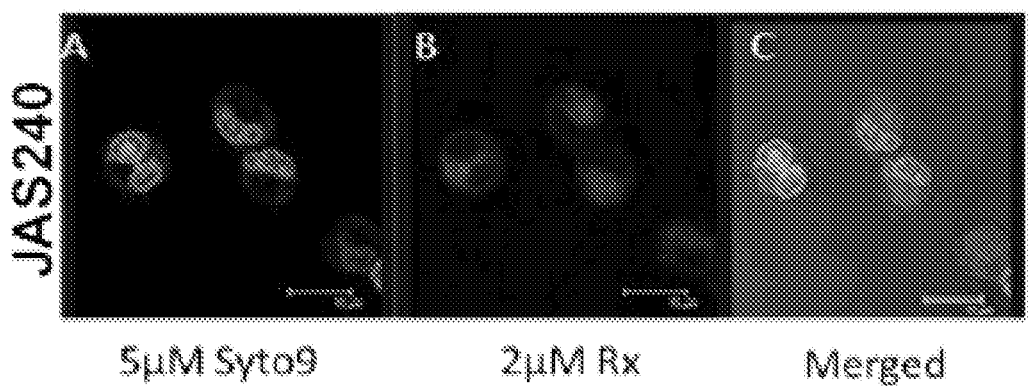
FIG. 5 illustrates that JAS240 is localized to the cytoplasm. Fluorescent confocal micrographs show MDA-MB-231 cells stained for 30 min with A) the nuclear stain SytoGreen, B) 2 µM JAS240 localized to the cytoplasm, and C) merged images.

FIG. 5 shows that JAS240 is localized to the cytoplasm. Fluorescent confocal micrographs show MDA-MB-231 cells stained for 30 min with A) the nuclear stain SytoGreen, B) 2 µM JAS240 localized to the cytoplasm, and C) merged images.

Figure 6:
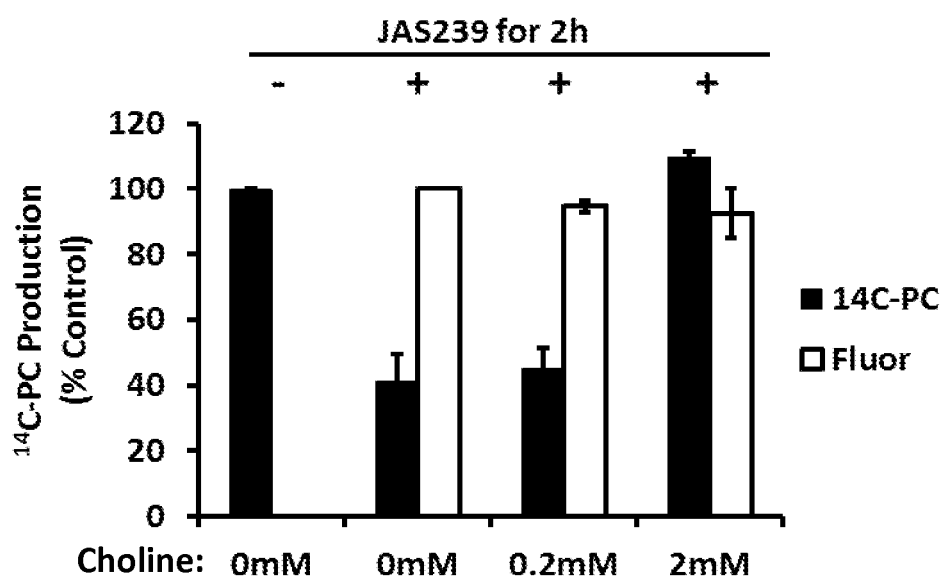
FIG. 6 depicts that JAS239 enters cells independent of choline transporters and is a competitive inhibitor of ChoK. MDA-MB-231 cells were treated for 2 hr with or without 10 µM JAS239 in the presence of varying concentrations of choline. Autoradiography was used to estimate phosphorylation of $^{14}$C-labeled choline. Fluorimetry was performed under the same cellular conditions for estimation of probe uptake (Excitation 640 nm, Emission 770 nm). These values represent a ratio of JAS239 treated vs. untreated cells, and are reported relative to control.

As shown in FIG. 6, JAS239 enters cells independent of choline transporters and is a competitive inhibitor of ChoK. MDA-MB-231 cells were treated for 2 hr with or without 10 µM JAS239 in the presence of varying concentrations of choline. Autoradiography was used to estimate phosphorylation of $^{14}$C-labeled choline. Fluorimetry was performed under the same cellular conditions for estimation of probe uptake (Excitation 640 nm, Emission 770 nm). These values represent a ratio of JAS239 treated vs. untreated cells, and are reported relative to control.

Figure 7:
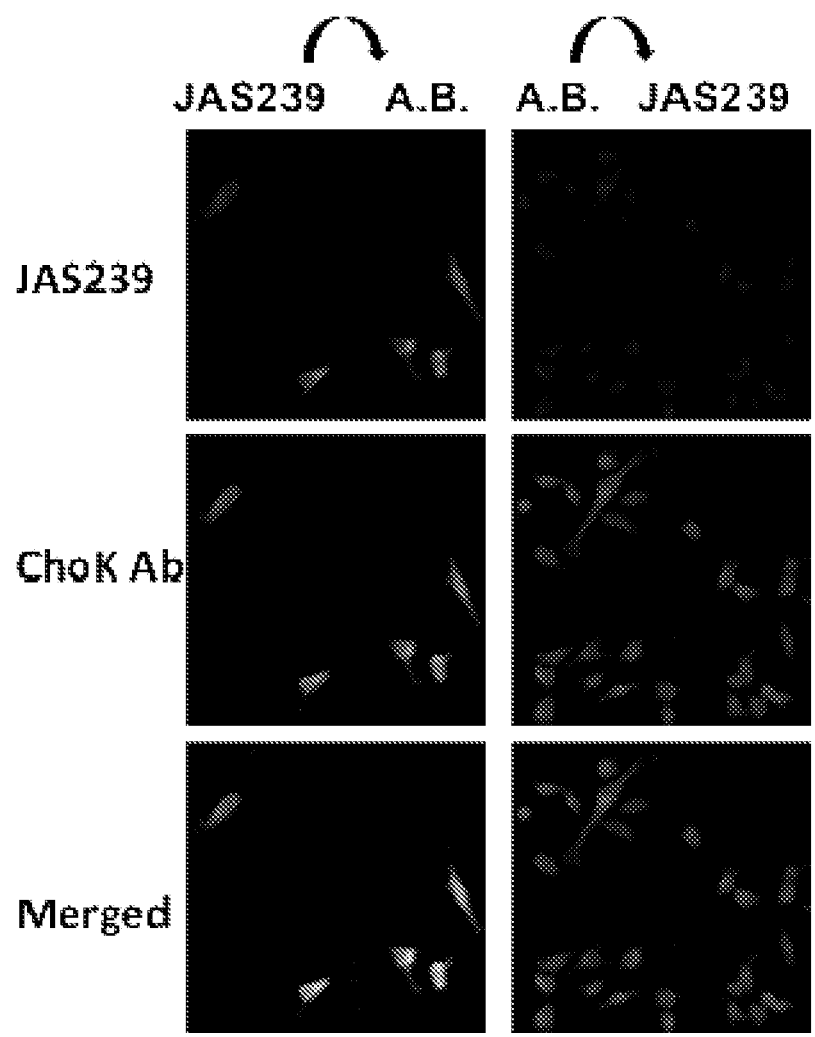
FIG. 7 shows that JAS239 binds selectively to ChoKα. Confocal microscopy images of fixed permeabilized MDA-MB-231 cells treated with 2 µM JAS239 prior to (Left) or following (Right) addition of ChoKα antibody. The merged Figure shows that JAS239 co-localizes with cytosolic expression of ChoKα. Prior treatment with ChoK antibody prevents JAS239 binding indicating selectivity of the compound for ChoK.

Immunofluorescence studies confirmed the specificity of ChoKα binding (FIG. 7). JAS239 added to MDA-MB-231 cells before ChoK antibody co-localizes with the cytosolic expression of ChoK (Left panels). Binding was reduced when cells were pretreated with the antibody that blocks access to the enzymatic active site (FIG. 7, right panels) indicating that binding of JAS239 is specific to ChoKα. Cells were treated with a Rabbit polyclonal antibody to human ChoKα followed by a Texas Red Goat Anti-Rabbit IgG secondary antibody. Confocal images were taken using a Leica DMI6000 B microscope with channels for Texas Red (Ex: 594 nm, Em: 600-630 nm), and JAS239 (Ex: 633 nm, Em: 728-800 nm).

Figure 8:
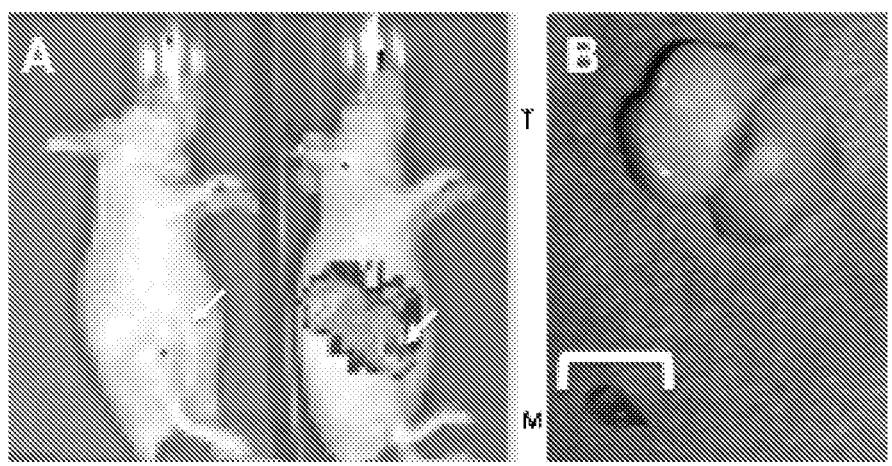
FIG. 8 shows MDA-MB-231 tumors (arrow) injected with 20 nmol of the fluorescent ChoK agonist JAS239. A) Left: Control. Right: Probe accumulates in kidney and tumor. B): Excised tissue shows tumor fluorescence and no background in muscle.

FIG. 8 shows the distribution of JAS239 in vivo. As shown in FIG. 8A, athymic nude mice were inoculated with MDA-MB-231 human breast cancer cells and after 2 wk injected i.v. with saline (control, left) or 20 nmol JAS239 in saline (right) and imaged for fluorescence (Ex. 745 nm; Em: 800 nm) 15 min post-injection in an IVIS Spectrum. The probe is demonstrated to accumulate in the kidneys and tumor. As shown in FIG. 8B, JAS239 accumulation within orthotopic breast tumors was confirmed in excised tissue using a dual CCD fluorescence camera. There was no fluorescence detectable from background muscle tissue (bottom left).

Figure 9:
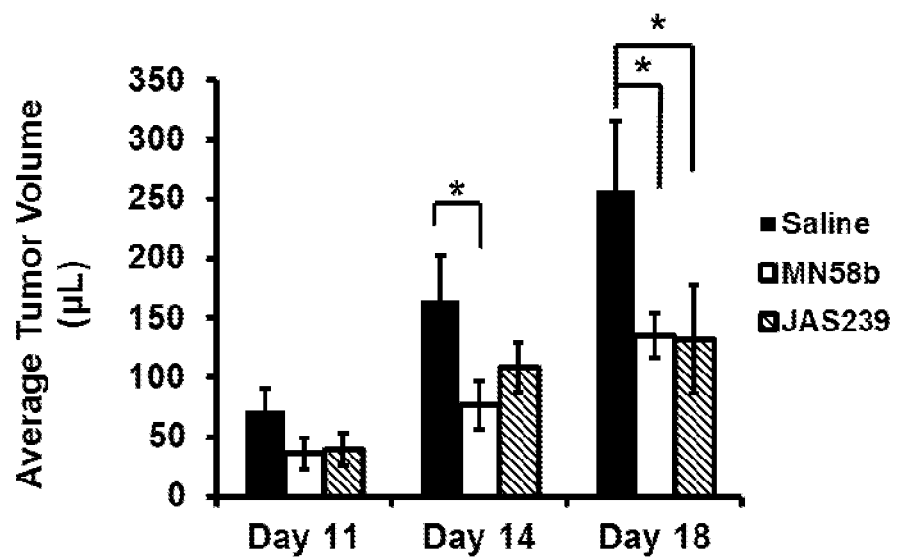
FIG. 9 demonstrates that JAS239 has therapeutic effects in MDA-MB-231 orthotopic tumors in nude mice and causes tumor growth delay at the same concentration as MN58b.

FIG. 9 shows the therapeutic potential of JAS239. MDA-MB-231 breast cancer cells were injected orthotopically into athymic nude mice. After two days of acclimation, mice were treated with 100 µL of either saline, 4 mg/kg MN58b, or 4 mg/kg JAS239 for five consecutive days i.p. (five mice per group). Tumor volumes were measured using a caliper and the formula: volume=length×width×height×π/6. Values represent the mean±standard deviation, and statistical significance calculated using a Student's T-Test *p<0.05. Both JAS239 and MN58b caused similar tumor growth delays at the same concentrations.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for diagnosing a cancer disease associated with choline kinase (ChoK), the method comprising: administering to a subject an effective amount of a composition comprising (a) an intrinsically fluorescent bis-heterocyclic choline kinase (ChoK) inhibitor compound in aqueous solution, said inhibitor having a structure of:

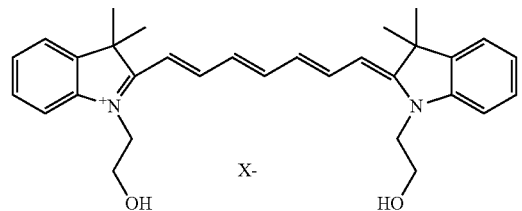

wherein X— is Cl— or Br— and (b) one or more pharmaceutically acceptable carriers; and detecting the fluorescence in said subject with an imaging device that measures the fluorescence in near infrared (NIR) range.

2. A method for treating a cancer disease associated with choline kinase (ChoK), the method comprising: administering to a subject an effective amount of a composition comprising (a) an intrinsically fluorescent bis-heterocyclic choline kinase (ChoK) inhibitor compound in aqueous solution, said inhibitor having a structure of:
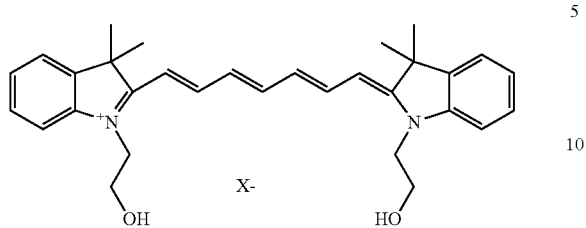
wherein X— is Cl— or Br— and (b) one or more pharmaceutically acceptable carriers.